(12) United States Patent
Ranalletta et al.

(10) Patent No.: US 7,892,210 B2
(45) Date of Patent: Feb. 22, 2011

(54) APPARATUS, METHOD AND SYSTEM FOR ADMINISTRATION OF IV LIQUID MEDICATION AND IV FLUSH SOLUTIONS

(75) Inventors: Joseph Ranalletta, Englewood, CO (US); Rob Brereton, Centennial, CO (US); Laura Zoerner, Highlands Ranch, CO (US); Brian Baldwin, Centennial, CO (US); Randall Wallace Smith, Lakewood, CO (US); Garrett L. Barker, Meridian, TX (US)

(73) Assignee: Baxa Corporation, Englewood, CO (US)

( * ) Notice: Subject to any disclaimer, the term of this patent is extended or adjusted under 35 U.S.C. 154(b) by 1484 days.

(21) Appl. No.: 11/242,618

(22) Filed: Oct. 3, 2005

(65) Prior Publication Data

US 2007/0088282 A1 Apr. 19, 2007

(51) Int. Cl.
*A61M 5/178* (2006.01)
(52) U.S. Cl. .................................. 604/184; 604/257
(58) Field of Classification Search .............. 604/184, 604/236, 207, 257, 246, 251
See application file for complete search history.

(56) References Cited

U.S. PATENT DOCUMENTS

| | | | |
|---|---|---|---|
| 3,344,785 A | 10/1967 | Hamilton | |
| 3,834,372 A | 9/1974 | Turney | |
| 4,210,173 A | 7/1980 | Choksi et al. | 137/512.3 |
| 4,219,021 A | 8/1980 | Fink | 128/214 |
| 4,253,501 A | 3/1981 | Ogle | 141/27 |
| 4,397,335 A | 8/1983 | Doblar et al. | 137/625.19 |
| 4,563,175 A | 1/1986 | Lafond | 604/155 |
| 4,645,496 A | 2/1987 | Oscarson | 604/248 |
| 4,713,060 A | 12/1987 | Riuli | 604/199 |
| 4,857,056 A | 8/1989 | Taloon | 604/135 |
| 5,002,528 A | 3/1991 | Palestrant | 604/28 |
| 5,104,387 A | 4/1992 | Pokorney et al. | 604/248 |

(Continued)

FOREIGN PATENT DOCUMENTS

WO WO 9934846 7/1999

OTHER PUBLICATIONS

Project Literature by GL Medical, the "Twist-N-Ject" Stopcock, 2 Pages.

(Continued)

*Primary Examiner*—Kevin C Sirmons
*Assistant Examiner*—Deanna K Hall
(74) *Attorney, Agent, or Firm*—Marsh Fischmann & Breyfogle LLP

(57) ABSTRACT

An improved apparatus, method and system are provided for medical liquid administration, including in particular liquid medication and/or flush solution infusions. The inventive apparatus includes a barrel, a plunger slidably disposed within the barrel and extending from a distal end thereof, and at least one medical liquid delivery line having a proximal end fixedly positioned relative to the barrel, wherein the medical delivery line is fluidly interconnectable proximal to the plunger and extends along at least a portion of the barrel and in a direction distally away from the distal end thereof. To accommodate the administration of both a liquid medication and flush solution, two coincidentally-positioned medical liquid delivery lines may be included, each of which may extend through the plunger to the valve. The valve may be positionable to accommodate the selective administration of a desired medical liquid through an interconnected catheter interconnection line.

55 Claims, 29 Drawing Sheets

U.S. PATENT DOCUMENTS

| | | | | |
|---|---|---|---|---|
| 5,144,972 | A | | 9/1992 | Dryden ........................ 137/15 |
| 5,176,658 | A | | 1/1993 | Ranford ...................... 604/247 |
| 5,318,539 | A | | 6/1994 | O'Neil ........................ 604/118 |
| 5,324,266 | A | * | 6/1994 | Ambrisco et al. ........... 604/125 |
| 5,336,188 | A | | 8/1994 | Kriesel ........................ 604/132 |
| 5,419,771 | A | | 5/1995 | Kriesel ........................ 604/132 |
| 5,439,452 | A | | 8/1995 | McCarty ..................... 604/186 |
| 5,454,792 | A | | 10/1995 | Tennican et al. ............ 604/191 |
| 5,518,005 | A | * | 5/1996 | Brannon ..................... 600/578 |
| 5,655,541 | A | | 8/1997 | Vattuone |
| 5,740,810 | A | | 4/1998 | Johnson et al. ............. 128/673 |
| 6,086,561 | A | | 7/2000 | Kriesel et al. ............... 604/133 |
| 6,457,488 | B2 | | 10/2002 | Loo .......................... 7/625.47 |
| 6,953,450 | B2 | | 10/2005 | Baldwin et al. ............. 604/248 |
| 2003/0055375 | A1 | | 3/2003 | Holst et al. .................... 604/67 |
| 2003/0181865 | A1 | | 9/2003 | Abrahamson et al. ....... 604/250 |
| 2003/0181866 | A1 | | 9/2003 | Abrahamson et al. ....... 604/250 |
| 2004/0039346 | A1 | * | 2/2004 | Baldwin et al. ............. 604/236 |
| 2004/0073192 | A1 | | 4/2004 | Flament-Garcia et al. ... 604/523 |
| 2005/0004530 | A1 | | 1/2005 | Grabenkort et al. ......... 604/218 |
| 2005/0051572 | A1 | | 3/2005 | Vogel et al. .................... 222/83 |
| 2005/0063831 | A1 | | 3/2005 | Fathallah et al. .............. 417/63 |
| 2005/0063847 | A1 | | 3/2005 | Fathallah et al. ......... 417/477.2 |

OTHER PUBLICATIONS

Product Instructions by Children's Medical Ventures, Inc., Safe-T-Care Anti-free flow Infusion / Flush Set, 1 Page.

Information Page by Children's Medical Ventures, Inc., Safe-T-Care Infusion Set, www.childmed.com, 2 page.

Product Literature by Needle & Infusion Technologies, Inc., Infucare Syringe Pump / Flush Extension Set for IV Medications, 1 Page.

Product Information Card by Baxter, Interlink Needle-Less IV Access System, 1 Page.

Information Page by Baxter, Interlink Needle-Less IV Access System, www.lifeassist.com, 37 Pages.

* cited by examiner

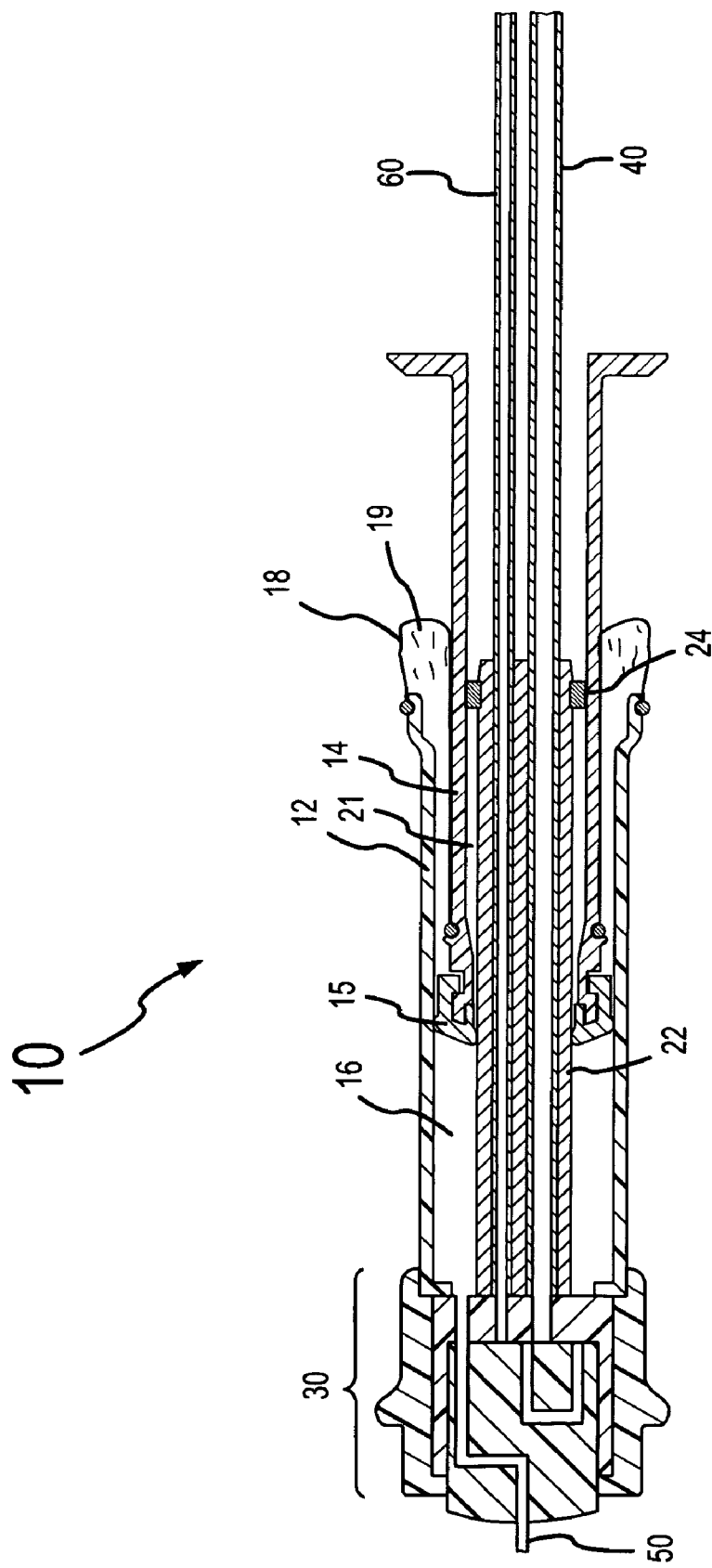

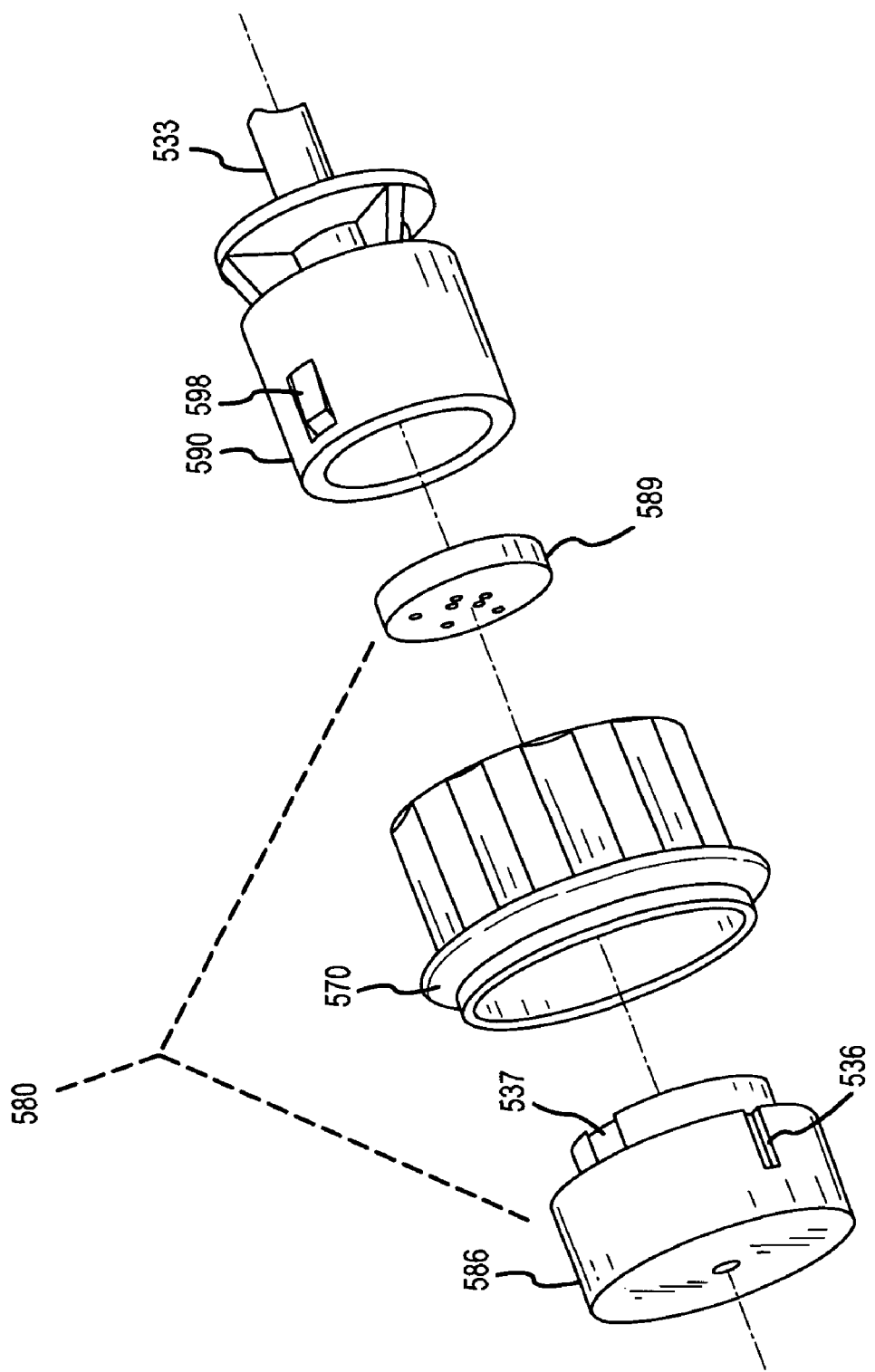

APPARATUS, METHOD AND SYSTEM FOR ADMINISTRATION OF IV LIQUID MEDICATION AND IV FLUSH SOLUTIONS

FIELD OF THE INVENTION

The present invention relates to the field of medical liquid administration, and more particularly, to an administration apparatus, method and system for administering multiple medical liquids during one or repeated periods. The administration apparatus, method and system are particularly apt for use in successive intravascular (IV) administrations of liquid medication and one or multiple flush solutions over an extended time period, wherein the liquid medication and flush solution(s) may be alternately infused through a single catheter fluid interconnection per sequence.

BACKGROUND OF THE INVENTION

Numerous techniques are employed for the administration of "medical liquids" (e.g. liquid medication and flush solutions) to a patient. In particular, where repeated medication infusions are required, medical liquids are often administered via the use of a vascular access catheter that is fluidly interconnected or interconnectable to one or more medical liquid sources via an associated tubing line set. Typically, the catheter is inserted into the vein of a patient and left there for multiple intravenous (IV) infusions during an extended course of medication therapy. By way of example, the time period between IV drug infusions may be between about 4 to 24 hours, wherein the IV liquid medication source is typically replaced after each dose infusion. In the course of extended medication therapy a given tubing line set may be repeatedly employed, and a number of tubing line sets may be successively employed. For example, it is typical to replace a given tubing line set every two or three days.

During extended therapy applications, a desirable practice is to disconnect the catheter from a medical liquid source and tubing line set between infusions. In this regard, most patients receiving IV medication therapy are ambulatory to some degree and benefit from not being continuously connected.

In conjunction with the repeated connection/disconnection of a catheter and liquid medication source and tubing line set, it is usual practice to purge the catheter with a flush solution (e.g. a saline solution) prior to and at the completion of a given liquid medication infusion. Pre-infusion flushing verifies that the catheter is primed and clear of obstructions. Post infusion flushing not only flushes through any remaining liquid medication to achieve the desired therapeutic effect, but also reduces any chance that the catheter may become blocked in-between infusions (e.g. by a blood clot that may otherwise form in the catheter. In relation to infusion procedures, it is also common practice to verify the proper functioning of a catheter via aspiration. This is typically done prior to pre-infusion flushing. The procedure entails using the flush solution syringe or liquid medication syringe to drain a small amount of a patient's blood through the catheter, thereby permitting visual verification of proper catheter functionality, then advancing the blood back through the catheter using the syringe. By way of example, such procedure assures that the catheter is not blocked by a blood clot and is otherwise properly inserted into a patient's vascular system.

A number of approaches are currently utilized for the noted flushing procedures. Such techniques generally entail the usage of flush solutions packaged in large volume, multi-dose reservoirs (e.g. about 250 ml. or more) or pre-filled unit dose syringes (e.g. having volumes of 2, 3, 5 or 10 ml.).

Where a unit dose syringe is utilized, medical personnel must generally remove the syringe from packaging, remove a cap from the syringe, remove any air in the syringe, swab a catheter access port with an antibacterial material, interconnect the syringe to a catheter access port, optionally aspirate the catheter, advance the syringe plunger to infuse the flush solution (e.g. at a rate of about 5 to 10 ml. over about 15 to 30 seconds), remove the syringe from the catheter access port and discard the used syringe with its wrapper. As may be appreciated, such steps may need to be repeated numerous times over the course of extended medication therapy (e.g. before and after each infusion and catheter access port reconnection), thereby entailing significant medical personnel time and resulting in substantial medical waste.

Where multi-dose flush solution reservoirs are employed, medical personnel typically utilize an empty unit dose syringe to draw the flush solution from the reservoir, and then follow the same basic procedure noted above in an administering the flush solution. Again, such procedure may be followed a number of times during a medication therapy. Further, contamination concerns may arise when a unit dose syringe is filled from a multi-dose reservoir at the point of use. To address such concern, unit dose syringes are often filled from a multi-dose reservoir within a pharmacy department of a medical care facility utilizing a HEPA-filter air hood. However, significant syringe handling is required. Moreover, labeling becomes a further need when a delay is expected between the filling of a unit dose syringe and the usage of the filled syringe.

SUMMARY OF THE INVENTION

In view of the foregoing, one objective of the present invention is to reduce the number of steps and associated time required by medical personnel for the infusion of medical liquids in conjunction with IV procedures. A related objective is to facilitate the utilization of multi-dose flush solution sources in conjunction with IV liquid medication administration procedures occurring over an extended course of therapy.

An additional objective of the present invention is to provide the noted medical liquid administration efficiencies in a manner that also enhances the maintenance of sterility.

A further objective of the present invention is to provide the noted medical liquid administration efficiencies in a compact manner that yields space efficiency. A related objective is to provide the noted medical liquid administration efficiencies in a streamlined manner to facilitate the maintenance of an organized patient care site.

Another objective of the present invention is to provide the noted medical liquid administration efficiencies in a manner that accommodates the maintenance of medical personnel control over the medical liquid administration process.

Yet another objective of the present invention is to reduce medical waste associated with the IV administration of flush solutions.

One or more of the above objectives and additional advantages may be realized by an inventive medical liquid administration apparatus that comprises a barrel having a proximal end and a distal end, and a plunger slidably disposed within the barrel and extending from the distal end thereof. The apparatus further includes at least a first medical liquid delivery line having a proximal end fixedly positioned relative to the barrel, wherein the first medical liquid delivery line is fluidly interconnectable to the barrel proximal to the plunger. Of note, the first medical liquid delivery line may be disposed to extend along at least a portion of the barrel and in a direction distally away from the distal end thereof for interconnection with a medical liquid source (e.g. a multi-dose flush solution source), thereby yielding a compact and streamlined apparatus that is capable of repeated use and that otherwise facilitates the maintenance of an organized patient care site.

In one aspect, the first medical liquid delivery line may extend through at least a portion of the plunger. More particularly, the first medical liquid delivery line may extend through the plunger from a proximal end to a distal end thereof, thereby enhancing the compact and streamlined appearance of the inventive apparatus. Further, at least a second medical liquid delivery line may be provided that extends through the plunger coincidental to the first medical liquid delivery line and distally away from the barrel in a streamlined manner, wherein the second medical liquid delivery line includes a proximal end fixedly positioned relative to the barrel. By way of example, a distal end of the first medical liquid delivery line may be interconnected or selectively interconnected to a flush solution source and a distal end of the second medical liquid delivery line may be interconnected or selectively interconnected to a liquid medication source, wherein the apparatus may be employed for the alternate flow of a flush solution and a liquid medication to a catheter or the like.

In one embodiment, a tubular member may be provided having at least a portion fixedly positioned within the barrel, wherein the first and/or second medical delivery lines are partially defined by and/or extend through at least a portion of the tubular member (e.g. from the proximal end to the distal end thereof). In turn, the plunger may be slidably disposed upon the tubular member. Correspondingly, a sealing member may be provided at the proximal end of the plunger and may comprise an outer seal ring and an inner seal ring for sealably engaging the internal surface of the barrel and the external surface of the tubular member, respectively. As may be appreciated, the above-noted features further contribute to a compact and streamlined apparatus.

In an alternative aspect, the barrel may comprise at least one passageway (e.g. in a sidewall thereof) that extends distally away from the proximal end thereof, wherein the passageway defines at least a portion of the first medical liquid delivery line. In this regard, the passageway may extend from the proximal end to the distal end of the barrel. Further, a second passageway may be provided in the barrel that defines a portion of a second medical liquid delivery line.

In another alternative aspect, the first medical liquid delivery line may be directly interconnected to and extend along the barrel. For example, the first medical liquid delivery line (e.g. a tubing line) may be interconnected to and extend along an external surface of the barrel. Further, at least a second medical liquid delivery line may also be directly interconnected to and extend along an external surface of the barrel.

In another aspect of the present invention, the apparatus may include a valve interconnected to the barrel and comprising a plurality of valve ports. In one approach, the valve is directly interconnected to the barrel, and the valve and barrel are coincidentally configured to further yield a compact and streamlined apparatus, as well as an apparatus having an overall appearance that tends to reduce undesired manipulation (e.g. by non-medical personnel) and otherwise facilitates the maintenance of an organized patient care site. That is, the valve may be configured to be disposed at least partially within and/or to extend from a proximal end of the barrel in a substantially conformal manner. For example, in arrangements where the valve extends proximally away from the proximal end of the barrel, the adjacent external surface portions of the valve and barrel may be coincidentally configured to present a streamline appearance. Stated differently, the barrel and valve may define partially overlapping and/or adjacent tubular volumes that are coincidentally shaped and preferably, substantially conformally shaped. Furthermore, the fluid interconnections between the barrel, the first and second medical liquid delivery lines and/or the catheter interconnection line may be included within such adjacent tubular volumes, such as between the proximal end of the valve and the proximal end of the plunger, to further yield a compact and streamlined apparatus.

As noted, the valve may include a plurality of ports, wherein a first valve port may be fluidly interconnectable to the barrel and a second valve port may be fluidly interconnectable to the proximal end of the first medical liquid delivery line. That is, when the valve is selectively positioned in a first valve position, the first valve port may be fluidly interconnected to the barrel (e.g. for flowing a medical liquid from the barrel to a patient via a catheter interconnection line). Alternatively, when the valve is selectively located in a second valve position, the second valve port may be fluidly interconnected to the proximal end of the first medical liquid delivery line (e.g. for flowing a medical liquid from the first medical liquid delivery line into the barrel).

In conjunction with this aspect, at least a second medical liquid delivery line may again be provided, wherein a proximal end of the second medical liquid delivery line is fixedly positioned relative to the barrel, and wherein the second medical liquid delivery line extends along at least a portion of the barrel and in a direction distally away from the proximal end thereof. In turn, the valve may be provided so that, when the valve is in the second valve position, the first valve port is fluidly interconnected to the proximal end of the second medical fluid delivery line (e.g. for flowing a medical liquid from the second medical liquid delivery line to a patient via a catheter interconnection line). Further, the valve may comprise a third valve port that is fluidly interconnected with the second valve port and that is fluidly interconnectable to the barrel (e.g. for flowing a medical liquid from the first medical liquid delivery line into the barrel in the second valve position).

In further relation to the above-noted aspect, the inventive apparatus may comprise a valve that is fluidly interconnected to the barrel and that includes a first set of ports (e.g., two or more ports) fixed relative to the barrel and a second set of ports that is movable relative to the first set of ports. More particularly, the first set of ports may include a first port fluidly interconnected to the barrel and a second port fluidly interconnected to the first medical liquid delivery line. Further, the second set of ports may comprise a first port that is fluidly interconnectable to the first port of the first set of ports, and a second port that is fluidly interconnectable to the second port of the first set of ports. Again, at least a second medical delivery line may be included. In turn, the first set of ports may further comprise a third port that is fluidly interconnected to the second medical liquid delivery line.

The second set of ports may further comprise a third port that is fluidly interconnected to a catheter interconnection line that extends in a direction proximally away from the proximal end of the barrel of the medical liquid administration apparatus. In one arrangement, the third port of the second set of ports may be fluidly interconnected to the first port of the first set of ports in a first valve position, and the third port of the second set of ports may be fluidly interconnected to the third port of the first set of ports in a second valve position. Further, the first and second ports of the second set of ports may be fluidly interconnected to the first and second ports of the first set of ports, respectively, in the second valve position.

In one arrangement, the valve may include a seat and a manifold, wherein one of the first set of ports and the second set of ports is disposed within the seat. More particularly, the seat may be fixedly interconnected to or within a proximal end of the barrel and the manifold may be movably disposed relative to the seat, wherein the first set of ports is disposed within the seat and the second set of ports is disposed within the manifold. As may be appreciated, the manifold may be selectively moved relative to the seat and barrel to establish a given desired one of a plurality of different valve positions noted hereinabove. In one approach, the manifold may be provided so that it is rotatable about a rotation axis wherein the ports of the first set and/or second set may be disposed in non-overlapping relation to the rotation axis of the manifold. The manifold may also be provided so that its rotation axis is coincidental with a center axis of the barrel of the medical liquid administration apparatus. In a related aspect, center axes of end openings of the ports comprising the first and/or second set of ports may be oriented coincidental (e.g., substantially parallel) to the center axis of the barrel. Additionally, the first medical liquid delivery may line extend along at least a portion of the barrel about an axis coincidental to the center axes of one or more of these end openings (e.g., coincidental to the center axes of the end openings of the ports of the first set of ports). Further, one of the ports of the second set of ports may include a proximal end opening interconnected to a catheter interconnection line, wherein a center axis of this proximal end opening may be coincidental to the barrel center axis and/or coincidental to the center axes of distal end openings of the ports of the first set of ports.

Further, center axes of distal end openings of the ports comprising the second set of ports may be coincidental to center axes of abutting, or interfacing, end openings of the ports comprising the first set of ports. As will be appreciated, each of the center axes of the end openings of the ports comprising the first and/or second set of ports may be coincidental with the barrel center axis irrespective of the valve position. That is, irrespective of whether the valve is in a first position (e.g., flush), second position (e.g., admin), third position (e.g., prime) or other valve position, the center axes of the end openings of the ports comprising the first and/or second set of ports may be coincidental with the barrel center axis. As will further be appreciated, the above-noted features further contribute to a compact and streamlined apparatus by providing a compact and streamlined fluid interconnection arrangement.

In a further related aspect, the valve may also be movable about a rotation axis, wherein the rotation axis is coincidental to the barrel center axis. Moreover, center axes of end openings of the ports of the first and/or second set of ports may be coincidental to this rotation axis. In one embodiment, a center axis of a proximal end opening of a port interconnected to a catheter interconnection line may be coincidental and/or co-axial with the rotation axis. In a related embodiment, the rotation axis may be co-axial with the barrel center axis. Further in this regard, center axes of end openings of the ports comprising the first set of ports may be coincidental to and non-overlapping with the rotation axis. In one embodiment, each of the ports of the first and second set of ports may be disposed within said valve in non-overlapping relation to the rotation axis. As will be appreciated, coinciding the various of axes of the apparatus, such as coinciding one or more of the barrel center axis, the valve rotation axis, an axis of extension of the first medical liquid delivery line, and center axes of end openings of the ports comprising the first and/or second set of ports, further contributes to a compact and streamlined apparatus.

In an additional aspect, the apparatus may include a valve fluidly interconnected to the barrel and a catheter interconnection line fluidly interconnected to the valve, wherein the valve is positionable in a plurality of valve positions. The valve may be provided so that, in a first valve position, a first flow path fluidly interconnects the barrel and the catheter interconnection line (e.g. for flowing a medical liquid from the barrel to a patient via the catheter interconnection line). Again, at least a second medical liquid delivery line may be provided, wherein a proximal end thereof is fixedly positioned relative to the barrel and the second medical liquid delivery line extends along at least a portion of the barrel and in a direction distally away from the proximal end thereof. In turn, the valve may be provided so that, in a second valve position, a second flow path fluidly interconnects the second medical liquid delivery line and the catheter interconnection line (e.g. for flowing a medical liquid from the second medical liquid delivery line to a patient via the catheter interconnection line). Further, the valve may be provided such that the first flow path and second flow path partially overlap (e.g. a portion of the first flow path is used in the second flow path).

In conjunction with this aspect, the apparatus may further include a visual indicator for providing a visual indication of the alternate positionability of the valve in the first valve position and the second valve position. By way of example, the visual indicator may comprise observable markings on the valve to indicate where the valve needs to be positioned to achieve a given mode of operation and to further indicate which given mode of operation the valve is currently positioned to perform. As may be appreciated, such given modes of operation may entail the selective flow of medical liquid into the barrel of the apparatus from a first medical liquid delivery line, the flow of medical liquid from the barrel of the apparatus through a catheter interconnection line, the flow of medical liquid through a second medical liquid delivery line to a catheter interconnection line and/or the flow of a medical liquid in the barrel of the apparatus through a second medical liquid delivery line.

In the latter regard, a valve of the inventive apparatus may be provided so that in a third valve position, a third flow path fluidly interconnects the barrel, the first medical delivery line and the second medical liquid delivery line (e.g. for use in priming the second medical liquid delivery line with a medical liquid (e.g. a flush solution) drawn into the barrel utilizing the plunger). Further, the valve may be provided so that the valve is not positionable in the noted third valve position after a first occurrence of such positioning. That is, once the valve has been positioned into the third position (e.g. for priming purposes) and then moved to another position, the valve may be provided so that it is not repositionable back into the third valve position. In conjunction with this feature, a visual indicator may again be provided, this time providing a visual indication of the alternate positionability of the valve in the first valve position, the second valve position and the third valve position. Further, the visual indicator may be provided so that it does not provide a visual indication of the positionability of the valve in the third valve position after a first occurrence of such positioning.

In relation to the above-noted aspects that relate to the inclusion of a valve in the inventive apparatus, such valve may comprise at least one component that is adapted for sequential movement relative to the barrel in two transverse planes to achieve positioning of the valve between at least a first and second alternate valve positions. By way of example, the moveable valve component may be adapted for sequential linear movement and rotational movement relative to the barrel for positioning the valve between first and second valve positions. In this regard, and in one embodiment, the apparatus may further include a biasing member for biasing the moveable component of the valve in a direction coincidental with one of the two transverse planes (e.g., either toward or away from the barrel). In turn, and by way of example, to achieve valve positioning a user may employ a pull and twist action. That is, the user may anchor the barrel of the apparatus with one hand and grasp a moveable valve component with another hand to pull the valve component away from the barrel (e.g. against the biasing force) and then rotate the valve component relative to the barrel to change from one valve position to another valve position. Alternatively, a user may use only one hand to move the valve, such as by anchoring the barrel with two or more fingers and pushing and turning the moveable valve component with a thumb.

In one arrangement, the valve may comprise a seat that is fixedly attached to the barrel, a valve housing that is axially and rotatably moveable relative to the seat and barrel, and a manifold that is disposed for co-rotation with the valve housing. To establish a desired valve position, the valve housing may be moved axially (e.g., against a spring-force of a biasing member), and then rotated with the manifold relative to the seat and barrel. As may be appreciated, the above-noted features yield an improved apparatus that facilitates enhanced medical personnel control over the administration of a medical liquid(s) since undesired and/or unintended operation of the apparatus is reduced.

In yet an additional aspect of the present invention, the inventive apparatus may comprise a barrel, a plunger and a first medical liquid delivery line as noted above, and may further include a tubular member that extends through at least a portion of the barrel, wherein the plunger may be slidably disposed on the tubular member. In this regard, a sealing member may be interconnected at a proximal end of the plunger, wherein the sealing member slidably engages an external surface of the tubular member and an internal surface of the barrel. As may be appreciated, the sealing member provides concentric seal rings (e.g. defining a doughnut-like configuration).

In one arrangement, the tubular member may be provided to define a proximal end portion of the first medical liquid delivery line. In another arrangement, the first medical liquid delivery line may be provided to extend through at least a portion of the tubular member.

In conjunction with this inventive aspect, a ring member may be fixedly interconnected about a distal end of the tubular member to slidably engage an internal surface of the plunger as the plunger is advanced/retracted relative to the barrel of the apparatus. As will be further described, the ring member provides a sterility-enhancing function by effectively scraping potential contaminants from the internal surface of the plunger. By way of example, the ring member may comprise a microbial barrier material (e.g. an open-cell or closed-cell foam or elastomer).

In further conjunction with the present aspect, the inventive apparatus may include a protective, flexible sheath that is interconnected to and continuously extends between the distal end of the barrel and the proximal end of the plunger, wherein the flexible sheath is adapted for co-movement with the plunger in a bellows-like fashion. For example, the flexible sheath may be ring-shaped, wherein the periphery of a central opening is sealably interconnected about a proximal end of the plunger and the outer periphery of the flexible sheath is sealably interconnected about or within the distal end of the barrel. As may be appreciated, the flexible sheath serves to maintain the sterility of the internal surface of the barrel.

Of additional note, an inner chamber may be defined by the flexible sheath, an internal surface of the barrel, an external surface of the plunger and a distal surface of the sealing member. Further, a plunger chamber may be defined by at least a proximal surface of the above-noted ring member, an internal surface of the plunger and an external surface of the tubular member. In such an arrangement, a passageway may be provided through the plunger to fluidly interconnect the inner chamber and the plunger chamber. In this regard, the plunger chamber, the noted passageway, and the inner chamber may define a closed system in which gas may flow between the plunger chamber and inner chamber via the passageway as the plunger is advanced and retracted relative to the barrel, thereby further enhancing the maintenance of sterility during use of the inventive apparatus. Further in this regard, the ring member of the plunger chamber may compromise a closed-cell film (e.g. a rubber material) to effect the closed system.

As may be appreciated, an inventive method for medical liquid administration to a patient is also provided. The inventive method includes the step of flowing a flush solution through a first medical liquid delivery line and into a barrel of a medical liquid apparatus, wherein the first medical liquid delivery line extends along at least a portion of the barrel and in a direction distally away from the distal end thereof. The method further comprises the step of removing at least a portion of the flush solution from the barrel through the valve by advancing a plunger relative to the barrel of the medical liquid administration apparatus, wherein the flush solution flows through the valve of the medical liquid administration apparatus.

In one aspect, the inventive method may further comprise the step of positioning the valve in a first valve position to complete at least a portion of the removing step, and positioning the valve in a second valve position. In the latter regard, the method may further comprise the step of passing a liquid medication through a second medical delivery line, the valve and a catheter interconnection line of the medical liquid administration apparatus with the valve in the second position. In conjunction with this aspect, at least a portion of the flowing step may be completed with the valve in the second valve position. Further, at least a portion of the flowing step may be completed with the valve in the second valve position, during the step of passing liquid medication through the second medical liquid delivery line.

In a further related aspect, the inventive method may include the steps of positioning the valve in a third valve position, wherein the removing step may further comprise the step of priming the second medical delivery line with the flush solution, with the valve in the third position, prior to the step of passing liquid medication through the second medical liquid delivery line.

As may be appreciated, after such priming step, the second medical delivery line may be interconnected to a source of liquid medication for subsequent passage through the second medical liquid delivery line, the valve and the catheter interconnection line of the medical liquid administration apparatus.

In one embodiment, the inventive method may comprise the additional steps of changing the position of the valve from the above-noted third valve position to one of the first and second valve positions after the step of priming the second medical delivery line, and then restricting the valve from being repositioned to the third valve position after such changing step.

In another embodiment, the inventive method may comprise the step of providing a visual indication on the medical liquid administration apparatus of the alternate positionability of the valve in the above-noted first valve position, second valve position, and third valve position. Further, the method may further provide for restricting the valve indication to the alternate positionability of the valve in the first and second valve positions after a first occurrence of the positioning of the valve in the third valve position.

In another aspect of the inventive method, the step of removing flush solution from the barrel of the medical liquid administration apparatus may comprise the step of priming a catheter interconnection line of the apparatus with the flush solution, with the valve in the above-noted first valve position, and prior to the passing step. In turn, the method may further include the step of interconnecting the catheter interconnection line to a catheter (e.g. interconnected to a patient) after the step of priming the catheter interconnection line and prior to the step of passing liquid medication through the second medical delivery line.

In yet another aspect of the inventive method, the catheter interconnection line of the medical liquid administration apparatus may be interconnected to a catheter (e.g. interconnected to a patient) prior to the step of passing liquid medication through a second medical liquid delivery line. In turn, the removing step may provide for flushing the catheter interconnection line and catheter with the flush solution, with the valve in the first valve position, either prior, after or both prior and after the step of passing the liquid medication to the second medical delivery line. Prior to the flushing step, the method may further provide for aspirating the catheter by retracting the plunger relative to the barrel of the medical liquid administration apparatus.

As may be appreciated, various features of the inventive apparatus discussed above may be utilized in conjunction with the inventive method. For example, at least a second medical delivery line may be provided to extend along at least a portion of the barrel and in a direction distally away from a distal end thereof. In this regard, first and second medical delivery lines may extend along the portion of the barrel in a coincidental manner. Further, the valve may be located at a proximal end of the barrel, wherein the catheter interconnection line is interconnected to and extends proximally away from the valve.

In yet a further aspect, the inventive method may comprise the step of moving at least one component of the medical liquid administration apparatus relative to the barrel, sequentially in two transverse planes, to change between the first and second valve positions noted hereinabove. More particularly, the removing step may comprise the steps of linearly moving a valve component relative to the barrel, and rotating the valve component relative to the barrel. In turn, the linearly moving step may provide for linear advancement or retraction of the valve component relative to the barrel along an axis that is coincidental with a center axis of the barrel. Further, the rotating step may provide for rotation of the valve component relative to the barrel upon an axis that is coincidental with the center axis of the barrel.

In yet an additional aspect, the inventive method may provide for interconnecting the first medical delivery line to a flush solution source prior to the flowing and removing steps, and repeating the removing step a plurality of times while maintaining the interconnection of the first medical liquid delivery line to flush solution source. Correspondingly, the method may include the step of restricting the flow of flush solution from the barrel and through the first medical liquid delivery line throughout the step of repeating the removing step.

As may be appreciated, an inventive system for administering a medical liquid to a patient is also provided. As will be appreciated, the inventive system may include any of the components discussed relative to the above-described inventive medical liquid administration apparatus and associated method. For example, the inventive system may include a barrel having a proximal end and a distal end, and a plunger slidably disposed within the barrel and extending from the distal end of the barrel. The system may further include a valve interconnected to a proximal end of the barrel. The system may also include a first medical liquid delivery line fixedly positioned relative to the barrel, where the first medical liquid delivery line extends along at least a portion of the barrel and in a direction distally away from a distal end of the barrel. The system may also include a second medical liquid delivery line extending along at least a portion of the barrel and in a direction distally away from the distal end of the barrel. The system may further include a catheter interconnection line fluidly interconnected to the valve, where the catheter interconnection line extends in a direction proximally away from the proximal end of the valve.

In one aspect, at least one of the first and second medical liquid lines extends along at least a portion of the barrel about an axis that is coincidental with the center axis of the barrel. In a related aspect, each of the first and second medical liquid delivery line may extend through a portion of the barrel to interconnect with the valve. In a further related aspect, the system may include a tubular member having a portion fixedly positioned within the barrel, where the plunger is slidably disposed on the tubular member, and where each of the first and second medical liquid delivery lines extends through at least a portion of the tubular member to interconnect with the valve. In an additional aspect, an end opening of a valve port fluidly interconnected to the catheter interconnection line may include a center axis that is coincidental with the center axis of the barrel.

In another aspect, the system may include a flush solution source connector interconnected to a distal end of the first medical liquid delivery line and a check valve interconnected to the first medical liquid delivery line to restrict flow of fluid back through the first medical liquid delivery line and flush solution source, the check valve being interconnected to the first medical liquid delivery line between the flush solution source connector and the proximal end of the first medical liquid delivery line. Additionally, a flush solution source (e.g., a multi-dose flush solution source) may be fluidly interconnected to the first medical liquid delivery line via the flush solution source connector. The system may further include a liquid medication connector interconnected to a distal end of the second medical liquid delivery line and a liquid medication source may be fluidly interconnected to the second medical liquid delivery line via the liquid medication connector. The system may also include a catheter connector interconnected to a proximal end of the catheter interconnection line and a catheter may be fluidly interconnected to the catheter interconnection line via the catheter connector.

Numerous additional aspects, features and advantages of the present invention will become apparent to those skilled in the art upon consideration of the further description that follows.

BRIEF DESCRIPTION OF THE DRAWINGS

FIG. 3a is a cross-sectional view a medical liquid administration apparatus of FIG. 1.

FIG. 5b is an exploded view of the valve embodiment of FIG. 5a.

FIG. 5e is a distal view of the seat of the valve embodiment of FIG. 5a.

FIG. 5f is a side view of the seat of the valve embodiment of FIG. 5a.

FIG. 5g is a cross-sectional view of the seat of the valve embodiment of FIG. 5a.

FIG. 5h is a proximal view of the gasket of the valve embodiment of FIG. 5a.

FIG. 5i is a side view of the gasket of the valve embodiment of FIG. 5a.

FIG. 5j is a distal view of the gasket of the valve embodiment of FIG. 5a.

FIG. 5k is a proximal view of the rigid manifold of the valve embodiment of FIG. 5a.

FIG. 5l is a side view of the rigid manifold of the valve embodiment of FIG. 5a.

FIG. 5m is a distal view of the rigid manifold of the valve embodiment of FIG. 5a.

FIG. 5n is a distal view of the valve housing of the valve embodiment of FIG. 5a.

FIG. 5o is a side view of the valve housing of the valve embodiment of FIG. 5a.

FIG. 5p is a proximal view of the valve housing of the valve embodiment of FIG. 5a.

FIG. 5q is a proximal, top-down view of the valve embodiment of FIG. 5a.

FIG. 7b is a perspective side view of one mode of operation of the valve in conjunction with the sensory indicator system and medical liquid administration apparatus of FIG. 7a.

DETAILED DESCRIPTION

Figure 1:
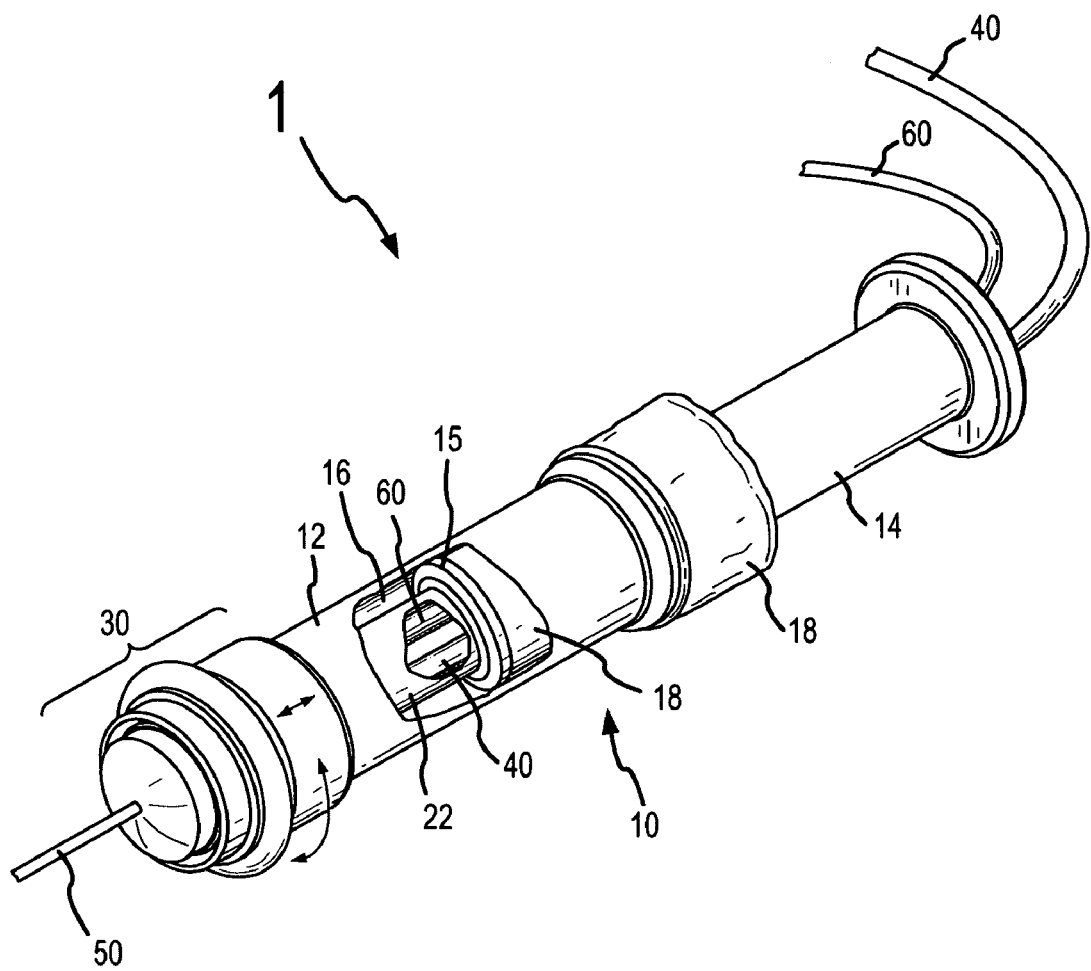
FIG. 1 is a perspective view of one medical liquid administration apparatus embodiment having a portion cut away to show internal features.
Figure 2:
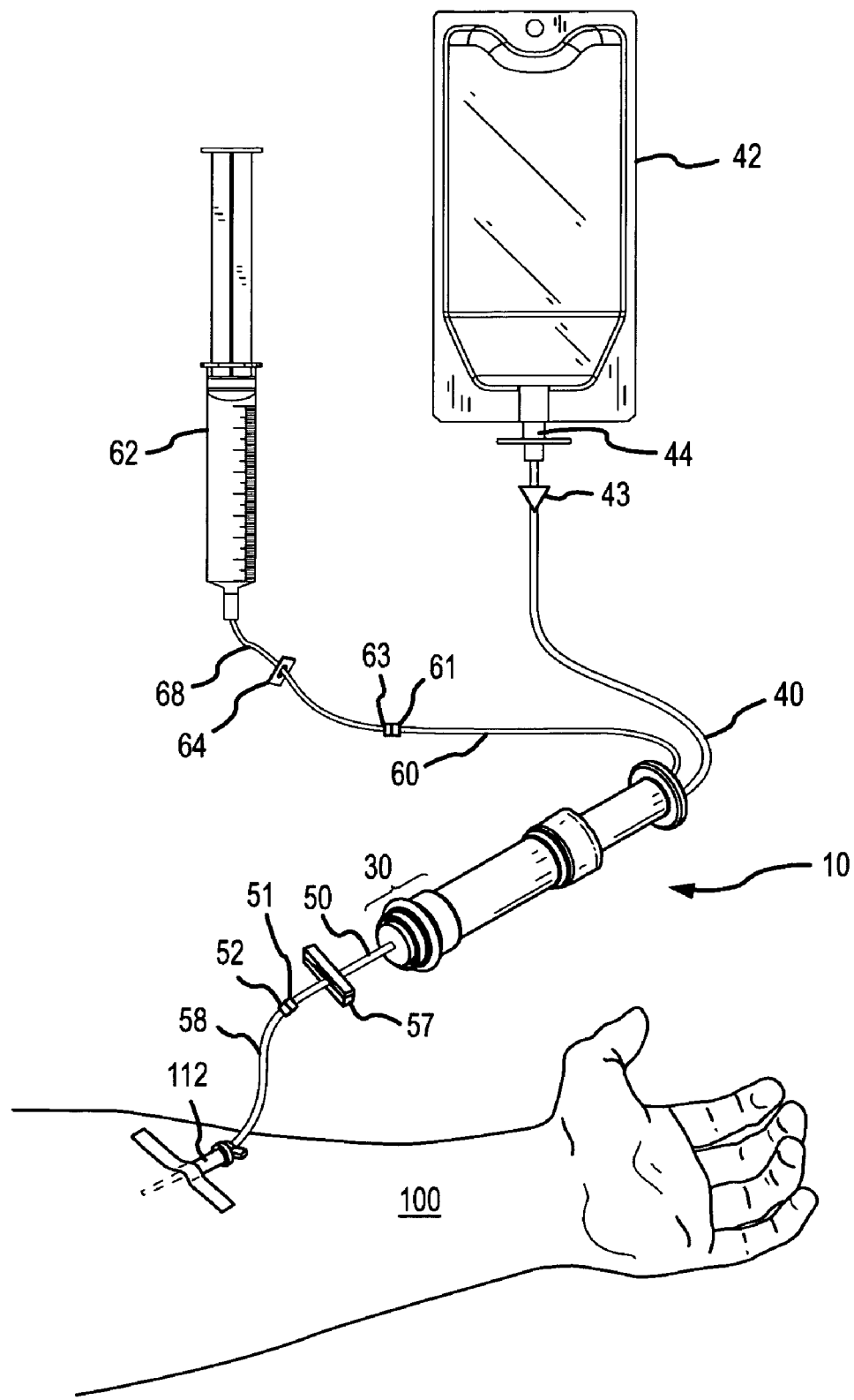
FIG. 2 is an environmental perspective view of the medical liquid administration apparatus of FIG. 1 as employed in one embodiment of a system for the administration of medical liquids.

Reference is now made to FIGS. 1 and 2, which illustrate one medical liquid administration apparatus embodiment comprising various features of the present invention. The administration apparatus 1 generally includes a syringe-like device 10, which includes a barrel 12 having a proximal end and a distal end, a plunger 14 slidably disposed in the barrel 12 and extending from the distal end of the barrel 12, and a valve 30 interconnected to the proximal end of the barrel 12. A first medical liquid delivery line 40 and a second medical liquid delivery line 60 are fluidly interconnectable to the valve 30 through plunger 14 and a tubular member 22 located in the barrel 12. As shown, the first and second medical liquid delivery lines 40, 60 extend distally from the distal end of the barrel 12 of administration apparatus 1. A fluid chamber 16 is located within the barrel 12 and may be at least partially defined by an internal wall of the barrel 12, an external wall of the tubular member 22, a distal face of the valve 30 and a proximal face of the plunger 14.

As shown in FIG. 2, the first medical liquid delivery line 40 may be selectively interconnected to a first medical liquid source 42 (e.g., a flush solution) and the second medical liquid delivery line 60 may be fluidly interconnected to a second medical liquid source 62 (e.g., liquid medication). As will be appreciated, the second medical liquid delivery line 60 may extend coincidental to the first medical liquid delivery line 40. As will further be appreciated, the first and second medical liquid delivery lines 40, 60 may extend along a portion of the barrel 12 about an axis that is coincidental to the center axis of the barrel 12.

A catheter interconnection line 50 may be fluidly interconnected or interconnectable to the valve 30 and may be selectively interconnected to a patient 100 (e.g. via catheter 112). The catheter interconnection line 50 may extend in a direction proximally away from the proximal end of the barrel 12.

Valve 30 includes a plurality of ports and passageways for accommodating the selective flow of medical liquids from medical liquid delivery lines 40, 60 to catheter interconnection line 50. In this regard, valve 30 may be moveable (e.g., rotatable) to position various ports of the valve 30 in relation to fluid chamber 16 and proximal ends of the first and second medical liquid delivery lines 40, 60 for selective flow of medical liquids through the valve 30. For example, and as discussed in further detail below, in a first valve position the fluid chamber 16 may be fluidly interconnected to catheter interconnection line 50 so that a first medical liquid (e.g., a flush solution from source 42) may be passed through a catheter 112 to a patient 100 (e.g., via advancement of the plunger 14). In a second valve position, the second medical liquid delivery line 60 may be fluidly interconnected to catheter interconnection line 50 so that a second medical liquid (e.g., a liquid medication from source 62) may be administered to a patient 100 (e.g., by a advancement of a syringe or operation of an autofusion pump). Also in the second valve position, the first medical fluid delivery line 40 may be fluidly interconnected to fluid chamber 16 (e.g., via a second flow path) for flowing the first medical liquid into the fluid chamber 16 (e.g., via retraction of the plunger 14). Thus, various flow paths through valve 30 may be selectively established. Such capability allows medical liquid administration apparatus 1 to be utilized for the administration of a plurality of medical liquids (e.g. via an interconnectable catheter 112).

Furthermore, the integration of syringe-like device 10 and valve 30 in medical liquid administration apparatus 1 facilitates the administration of a medical liquid from one or a plurality of interconnected sources (e.g. containing different medical liquids) on a successive, repeated basis during the course of medication therapy for a given patient. In particular, medical liquid administration apparatus 1 may be employed for the successive administration of a catheter flush solution, such as a saline solution and/or heparin solution, before and/or after liquid medication infusions, wherein at least one of the flush solutions is contained in an interconnectable reservoir of sufficient volume to dispense multiple flush solution dosages.

As noted, the medical liquid delivery lines 40, 60 may be disposed within the barrel 12 and plunger 14 to interconnect with valve 30. More particularly, the first and second medical liquid delivery lines 40, 60 may extend in a distal direction from the valve 30 through tubular member 22, through plunger 14 and exit the distal end of the plunger 14. As noted, plunger 14 may be slidably disposed in the barrel 12, thereby allowing a medical liquid to be drawn into fluid chamber 16 by retraction of the plunger 14 and administered to a patient from fluid chamber 16 by advancement of the plunger 14. In this regard, and with reference to FIGS. 3a-3b, plunger 14 may be slidably disposed on tubular member 22 and includes sealing member 15 to assist in sealing fluid chamber 16. As shown, sealing member 15 may be located on the proximal end of the plunger 14 and is adapted to sealably engage both an internal surface of barrel 12 and an external surface of the tubular member 22. Thus, sealing member 15 includes at least two sealing radii to affect the sealing of fluid chamber 16 (e.g., (a) an outer radius for engaging an internal surface of the barrel 16 and (b) an inner radius for engaging an external surface of the tubular member 22. In other words, sealing member 15 includes at least two concentric seal rings (e.g., a doughnut-like configuration) to effect sealing of fluid chamber 16. As will be appreciated, sealing member 15 may comprise a polymer-based material (e.g., a thermoplastic elastomer).

To facilitate repeated use of the syringe-like device 10 during a given medical therapy, a flexible sheath 18 may be provided for maintaining the sterility of fluid chamber 16. More particularly and with reference to FIGS. 3a-3b, flexible sheath 18 may be interconnected about the distal end of the barrel 12 and about the proximal end of the plunger 14. Further, the flexible sheath 18 may be ring-shaped, where the periphery of a central opening is sealably interconnected about a proximal end of the plunger and the outer periphery of the flexible sheath 18 is sealably interconnected about or within the distal end of the barrel (e.g., via elastomeric securing rings 26, 27 positioned about distal end of barrel 12 and the proximal end of the plunger 14, respectively). By way of example, flexible sheath 18 may comprise a polymeric material in the form of an extendable membrane that may continuously extend between distal end of the barrel and proximal end of the plunger, where the flexible sheath 18 functions in a bellows-like manner to accommodate advancement and retraction of plunger 14 relative to barrel 12. As will be appreciated, the flexible sheath 18, an internal surface of the barrel 12, an external surface of said plunger and a surface of said sealing member 15 may define an inner chamber 19. As the plunger 14 is retracted, the inner chamber 19 may be increasingly defined by the flexible sheath 18, and as the plunger is advanced, the inner chamber 19 may be decreasingly defined by the flexible sheath 18.

To further facilitate repeated use of the syringe-like device 10, the tubular member 22 may include ring member 24, which may be disposed to slidably engage an internal surface of plunger 14. More particularly, the ring member 24 may be fixedly interconnected about the distal end of the tubular member 22 and slidably and sealably interconnected with an internal surface of the plunger 14. As will be appreciated, as the plunger 14 is advanced and retracted in relation to the tubular member 22, the ring member 24 assists in maintaining the sterility of the external surfaces of the tubular member 22 by substantially removing contaminants (e.g., such as by scraping) located on an internal surface of the plunger 14 before those internal surfaces fluidly communicate with external surface of the tubular member 22. Further, the ring member 24 may be an open-cell material adapted to form a microbial barrier between internal surfaces of the plunger 14 and external surfaces of the tubular member 22. As will be appreciated, the use of an open cell material allows gas to pass through the ring member 24 so that the plunger 14 may be readily advanced and retracted while providing a degree of filtration to enhance sterility.

Figure 3B:
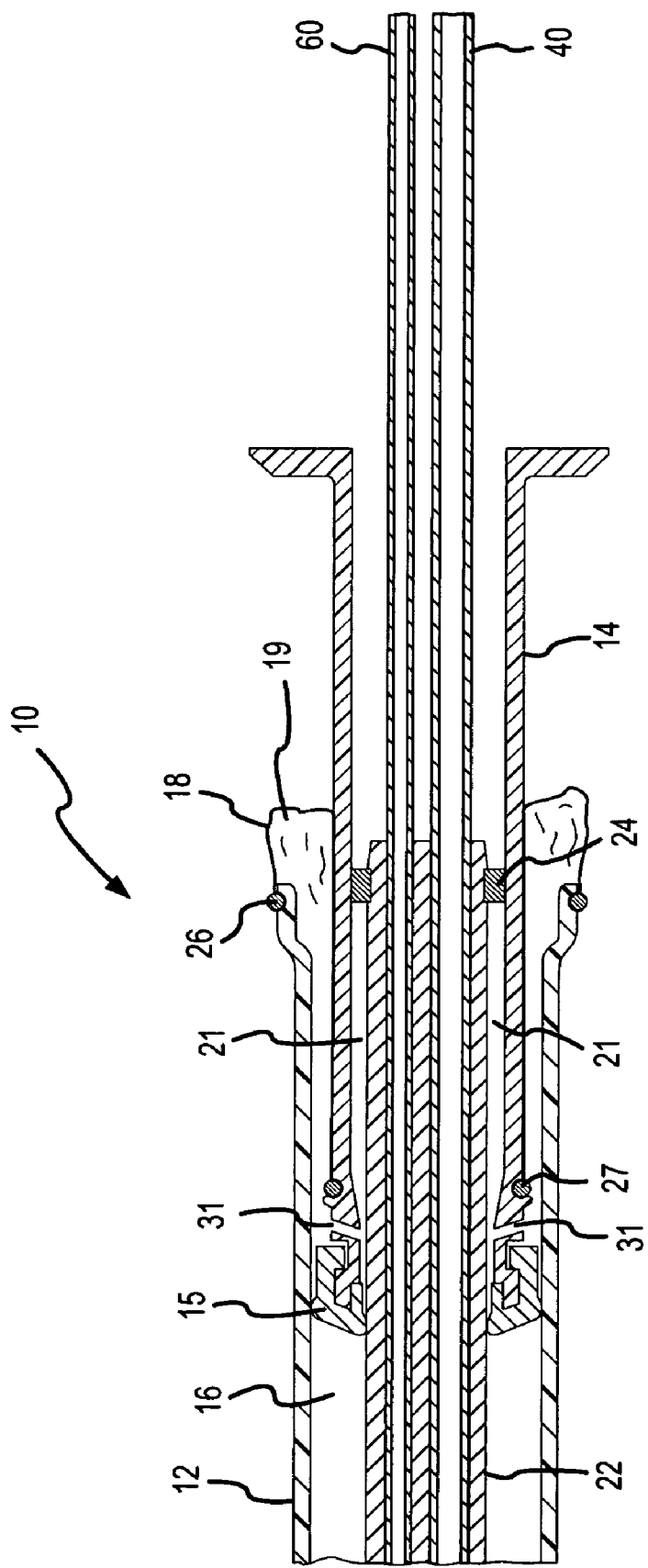
FIG. 3b is a cross-sectional side view of a distal portion of a medical liquid administration apparatus of FIG. 1 illustrating an optional passageway embodiment.

In a particular embodiment, as illustrated in FIG. 3b, an optional passageway 31 interconnecting a plunger chamber 21 to inner chamber 19 may be provided to further assist in maintaining the sterility of the syringe-like device 10. In the illustrated embodiment, the plunger chamber 21 is defined by an internal surface of the plunger 14, an external surface of the tubular member 22, a distal surface of the sealing member 15, and a proximal surface of the ring member 24. As the plunger 14 is advanced, the plunger chamber 21 is increasingly defined by an internal surface of the plunger 14 and an external surface of the tubular member 22, and as the plunger is retracted, the plunger chamber 21 is decreasingly defined by an internal surface of the plunger 14 and an external surface of the tubular member 22.

As will be appreciated, interconnecting inner chamber 19 to plunger chamber 21 via passageway 31 enables displacement of fluid (e.g., air or an inert gas) within the inner chamber 19 to the plunger chamber 21 upon advancement of plunger 14 and corresponding displacement of fluid within plunger chamber 21 to inner chamber 19 upon retraction of plunger 14. Thus, inner chamber 19, passageway 31 and plunger chamber 21 may define a closed system, which may assist in maintaining the sterility of the fluid chamber 16 by restricting such fluid chamber 16 from fluidly communicating outside thereof. In this regard, it will be appreciated that the ring member 24 may comprise a closed-cell material or an elastomer to achieve the desired closed system. Moreover, while the above embodiment is described in relation to a single passageway, a plurality of passageways may be utilized.

Referring now back to FIG. 2, the catheter interconnection line 50 may be interconnected to the valve 30 and a patient 100 for delivery of a medical liquid to the patient 100. The catheter interconnection line 50 may be interconnected to the valve 30 by any known means. The catheter interconnection line 50 may also be interconnected to the patient 100 by any known means. By way of illustration, the catheter interconnection line 50 may be interconnected to a patient 100 via female luer connector 51, male luer connector 52, tubing line 58 and catheter 112. In one embodiment, a distal end of the catheter interconnection line 50 may be fixedly interconnected to the syringe-like device 10 and a proximal end of the catheter interconnection line 50 may be fixedly interconnected to a luer connector 51 (male or female), and the medical liquid administration apparatus 1 may be shipped in such an arrangement. Various methods and apparatus for interconnecting a catheter interconnection line to a catheter are disclosed in commonly-owned U.S. Patent Publication No. 20040039346, the contents of which are incorporated herein by reference in their entirety. Clamp 57 may also be disposed about catheter interconnection line 50 and used to occlude catheter interconnection line 50 as necessary during treatment of a patient 100.

As noted, the first medical liquid delivery line 40 may be selectively interconnected to a first medical liquid source 42 (e.g., a multi-dose flush solution source) and the second medical liquid delivery line 60 may be selectively interconnected to a second medical liquid source 62. As will be appreciated, the medical liquid delivery lines 40, 60 may be selectively interconnected to the medical liquid sources 42, 62, respectively, by any known means, such as by direct connection, a spike member, or complementary luer connectors. Various methods and apparatus for interconnecting medical liquid delivery lines to various medical liquid sources are discussed in commonly-owned U.S. Patent Publication No. 20040039346.

It will be appreciated that any of the medical liquid delivery lines 40, 60 and/or catheter interconnection line 50 may be interconnected immediately prior to use, such as at the administration facility (e.g., a hospital) or may be interconnected during manufacture of the administration apparatus 1. In this regard, it may be appreciated that the medical liquid administration apparatus 1 may be shipped with the medical liquid delivery lines 40, 60 and/or the catheter interconnection line 50 interconnected to the valve 30. Also in this regard and as noted above, it will be appreciated that the apparatus 1 may include the valve 30 oriented in a shipping position (e.g., the below-described prime position). Furthermore, the administration apparatus 1 may be packaged in a sterile condition. For example, the administration apparatus 1 may be assembled, packaged in a heat-sealed enclosure, and sterilized via exposure to gamma radiation.

In one embodiment and with further reference to FIG. 2, a proximal end of the first medical liquid delivery line 40 may be fixedly interconnected to the syringe-like device 10, the distal end of the first medical liquid delivery line 40 may be fixedly interconnected to a spike member 44, and the medical liquid administration apparatus 1 may be shipped in such an arrangement. In a related embodiment, a proximal end of the second medical liquid delivery line 60 may be fixedly interconnected to the syringe-like device 10, the distal end of the second medical liquid delivery line 60 may be fixedly interconnected to a luer connector 61 (male or female) and the medical liquid administration apparatus 1 may be shipped in such an arrangement.

Referring now to FIGS. 4a-4h, one embodiment of the valve 30 is described. The valve 30 generally includes a valve housing 70, a manifold 80 and a seat 90. In the illustrated embodiment, the seat 90 is fixedly interconnected to the barrel 12 and valve housing 70 and manifold 80 are interconnected and adapted for co-movement relative to seat 90. More particularly, the valve housing 70 and the manifold 80 are mounted relative to the seat 90 for co-rotation about and co-rotation within the seat 90, respectively. The valve 30 may also include a first set of ports fixed relative to the barrel 12 and a second set of ports moveable relative to the first set of ports. For example, the first set of ports may be disposed within the seat 90 and a second set of ports may be disposed within the manifold 80. As is discussed in further detail below, the valve 30 may be rotated to three different positions to align various ports of the second set of ports with various ports of the first set of ports to allow selective flow of medical liquids through the apparatus 1.

More particularly, a first valve position may correspond to a "flush" position where the valve 30 and fluid chamber 16 may be oriented such that a medical fluid in the fluid chamber 16 may be flowed through the valve 30 and to catheter interconnection line 50. A second valve position may correspond to an "admin" position where the valve 30 and second medical liquid delivery line 60 may be oriented such that a medical fluid from the second medical fluid delivery line 60 may be flowed through the valve 30 and to a patient 100. Also in the "admin" position, the valve 30, first medical liquid delivery line 40 and fluid chamber 16 may be oriented such that a medical fluid from the first medical liquid delivery line 40 may be flowed through the valve 30 and to the fluid chamber 16. A third valve position may correspond to a "prime" position, where the valve 30, first and second medical liquid delivery lines 40, 60 and fluid chamber 16 may be oriented such that a medical liquid may be flowed through the first medical liquid delivery line 40 and the valve 30 to fill the fluid chamber 16 and second medical liquid delivery line 60. It will be appreciated that the above-described first, second and third valve positions are utilized for illustration purposes and are not meant to be limiting in any regard. That is, the above-described first, second and third valve positions are not meant to imply the position in which the valve 30 is shipped, the order in which the valve 30 is utilized or limit the number of valve positions, among others.

Figure 4A:
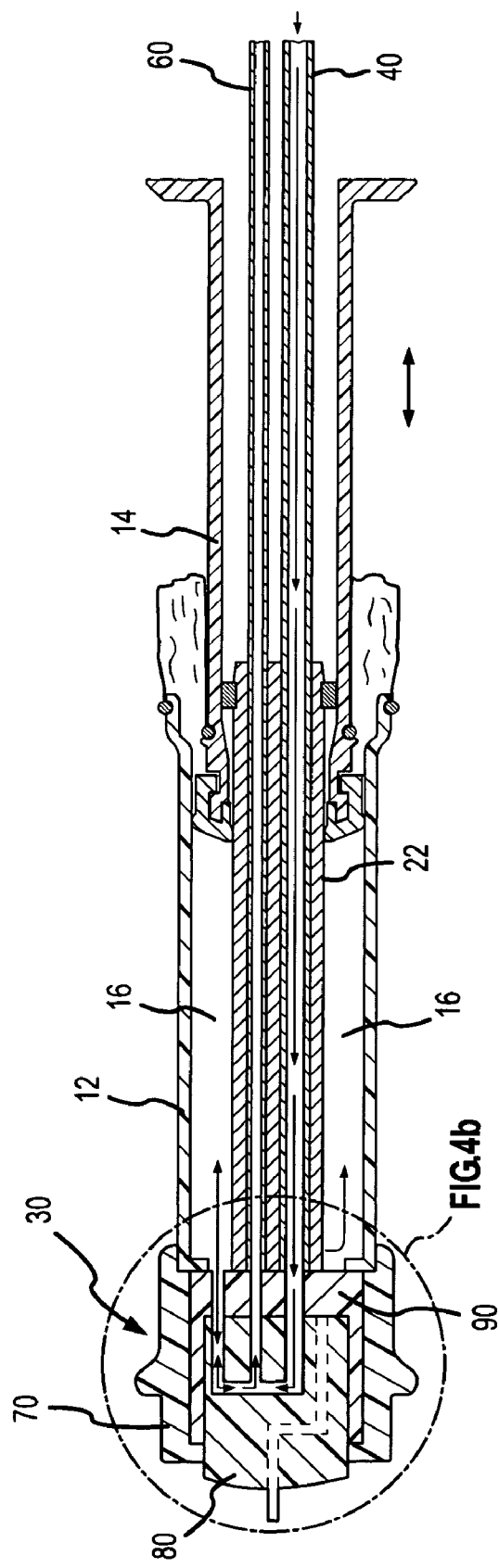
FIG. 4a is a cross-sectional side view of the medical liquid administration apparatus of FIG. 1 having a valve in a first position.
Figure 4B:
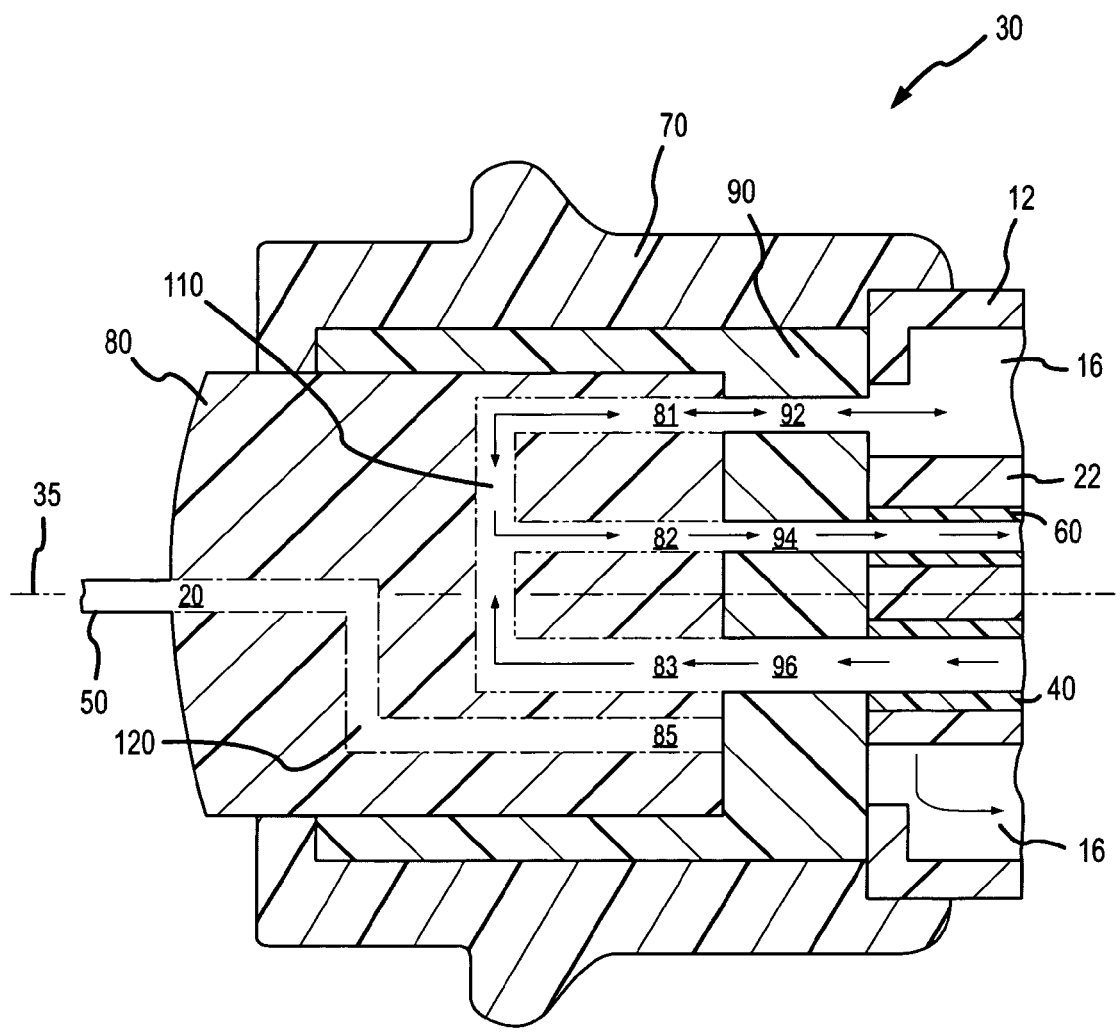
FIG. 4b is a cross-sectional side view of the valve of FIG. 4a and associated interconnections and flow paths.

Referring now to FIGS. 4a-4b, which illustrates one embodiment of the valve 30 in a prime position, manifold 80 may include manifold ports 81, 82, 83 and corresponding passageway 110. The seat 90 may include seat ports 92, 94, 96, which may be fluidly interconnected to the fluid chamber 16, the second medical liquid delivery line 60 and the first medical liquid delivery line 40, respectively. When the valve 30 is in a prime position, manifold ports 81, 82, and 83 may be aligned with abutting seat ports 92, 94, and 96, respectively, to allow flow of a medical liquid (e.g., a flush solution) through the first medical liquid delivery line 40 and into the fluid chamber 16 and second medical liquid delivery line 60 via passageway 110. More particularly, when plunger 14 is retracted relative to the barrel 12, a medical liquid may flow through first medical liquid delivery line 40, seat port 96, manifold port 83, passageway 110, manifold port 81, and seat 92 to fill fluid chamber 16 with a medical liquid. In this regard, seat ports 92 and 94, manifold ports 81 and 83 and passageway 110 define a first flow path.

Subsequently, the plunger 14 may be advanced relative to the barrel 12 and a portion of a medical liquid in the fluid chamber 16 may be removed therefrom and flowed through seat port 92, manifold port 81, passageway 110, manifold port 82, seat port 94 and into the second medical liquid delivery line 60. In this regard, seat ports 92 and 94, manifold ports 81 and 82 and passageway 110 define a second flow path. As will be appreciated, a one-way check valve 43 (see FIG. 2) may be utilized on the first medical liquid delivery line 40 to restrict the medical fluid in fluid chamber 16 from flowing back through the first medical liquid delivery line 40 during advancement of the plunger 14.

As illustrated in FIG. 4b, manifold 80 may further include manifold ports 20, 85 and corresponding passageway 120, but manifold port 85 may not be aligned with any of seat ports 92, 94, 96 in a prime position. Thus, flow of medical liquids through catheter interconnection line 50 and to a patient 100 may not be possible in a prime position. However, and as described in further detail below, valve 30 may be rotated to another position to position manifold port 85 in relation to various seat ports to allow flow of medical liquids through the apparatus 1.

Figure 4C:
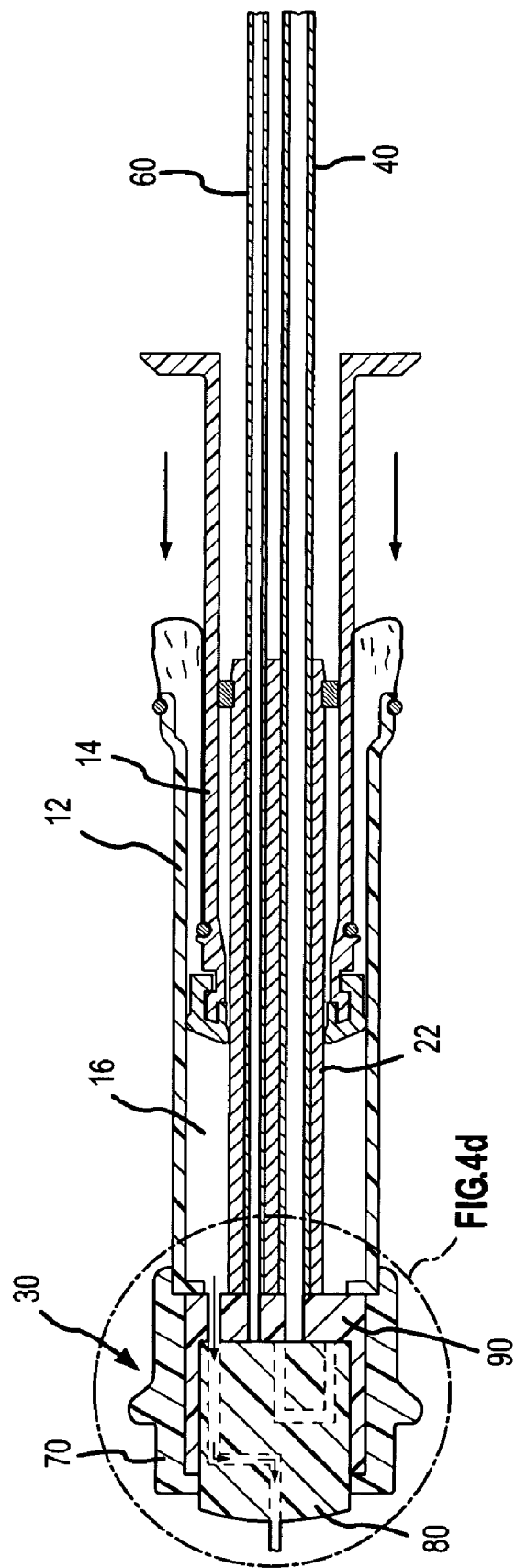
FIG. 4c is a cross-sectional side view of the medical liquid administration apparatus of FIG. 1 having a valve in a second position.
Figure 4D:
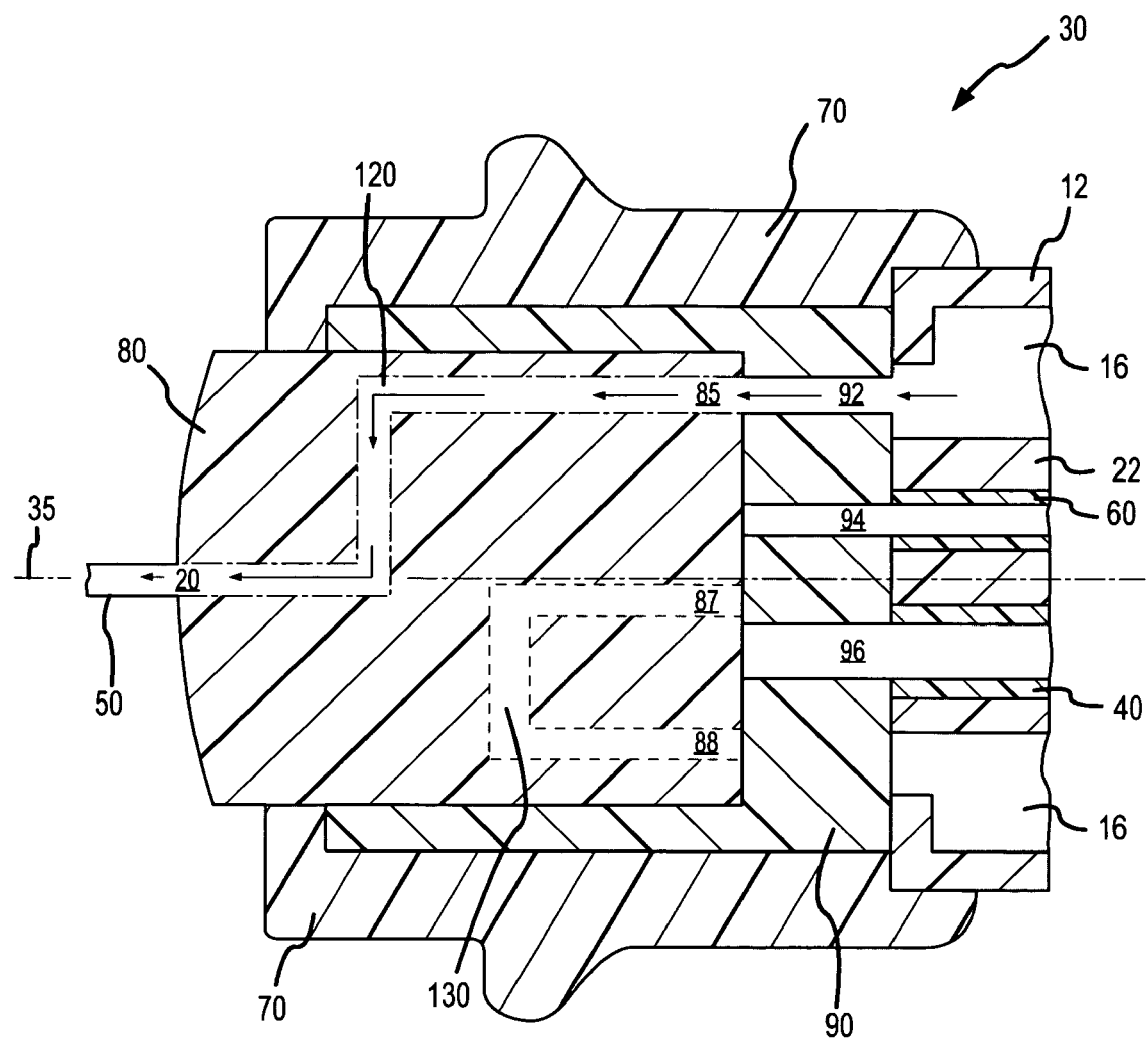
FIG. 4d is a cross-sectional side view of the valve of FIG. 4c and associated interconnections and flow paths.

For example and with reference to FIGS. 4c-4d, which illustrates one embodiment of the valve 30 in a flush position, manifold port 85 may be aligned with abutting seat port 92 when the valve 30 is in a flush position, thereby allowing a medical liquid in the fluid chamber 16 (e.g., a flush solution) to flow through the valve 30, catheter interconnection line 50 and, ultimately, to a patient 100. That is, when the valve 30 is in a flush position, a third flow path defined by seat port 92, manifold port 85, passageway 120 and manifold port 20 may be established, and this third flow path may allow flow of a medical liquid in the fluid chamber 16 to flow to a patient 100. More particularly, the plunger 14 may be advanced relative to the barrel 12 and a portion of a medical liquid in the fluid chamber 16 may be removed therefrom and flowed through the valve 30, via the third flow path, and through catheter interconnection line 50.

Figure 4E:
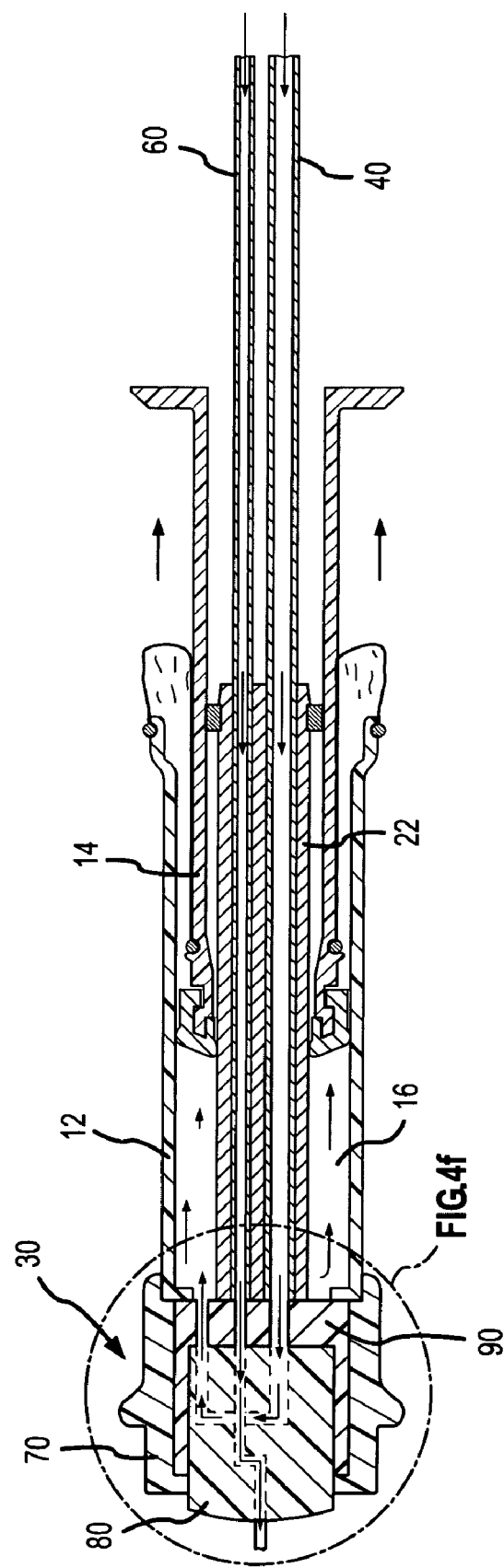
FIG. 4e is a cross-sectional side view of the medical liquid administration apparatus of FIG. 1 having a valve in a third position.
Figure 4F:
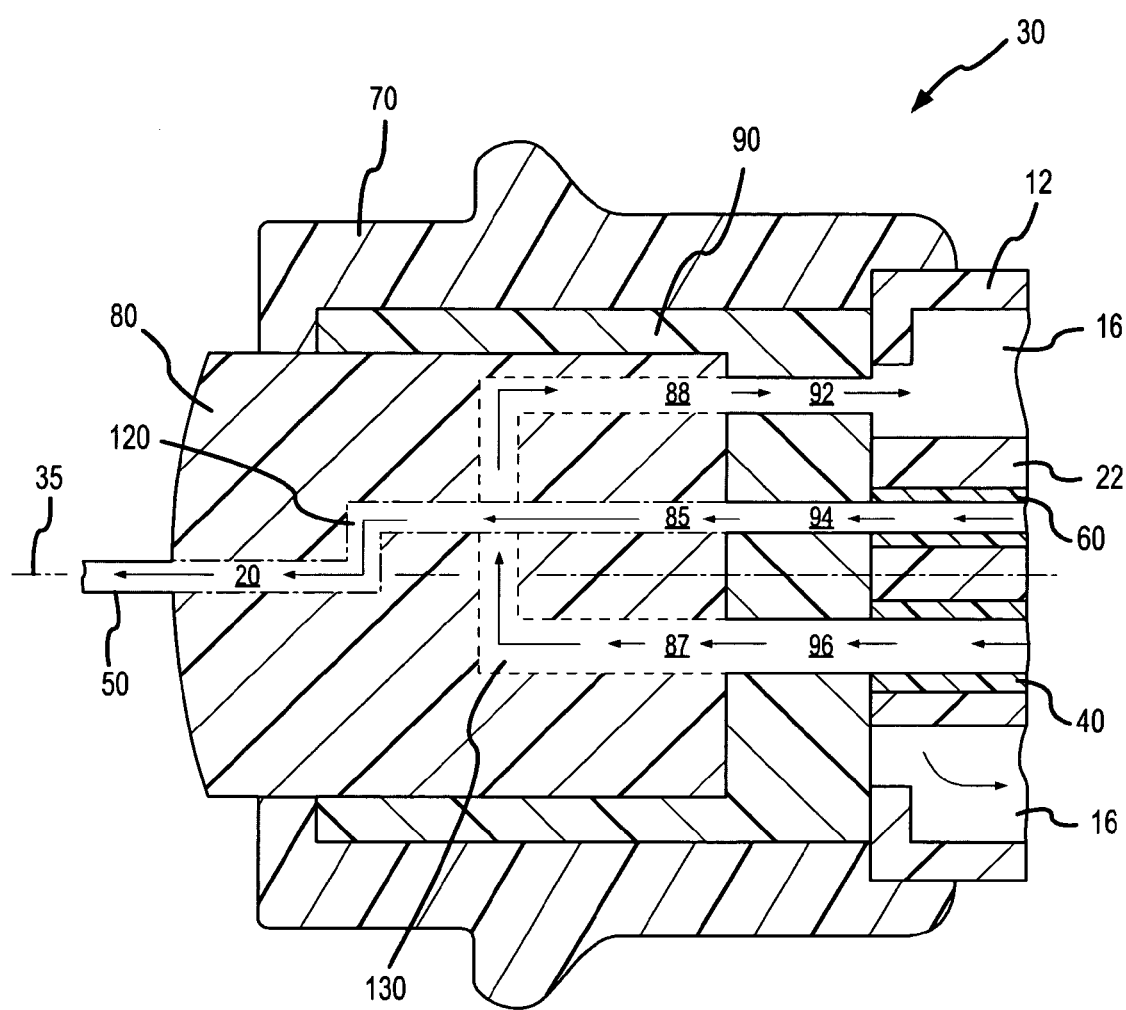
FIG. 4f is a cross-sectional side view of the valve of FIG. 4e and associated interconnections and flow paths.
Figure 4G:
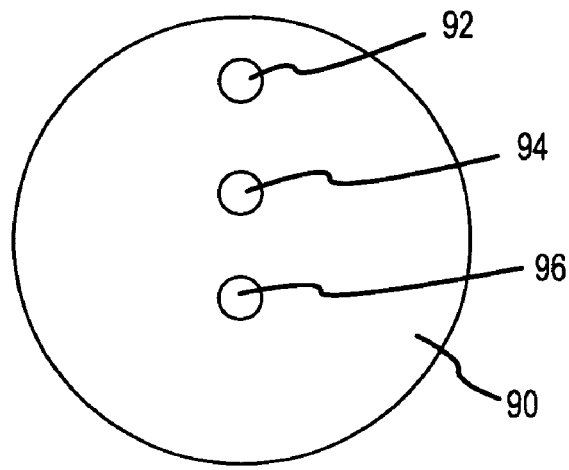
FIG. 4g is a distal view of a seat of the medical liquid administration apparatus of FIG. 1.
Figure 4H:
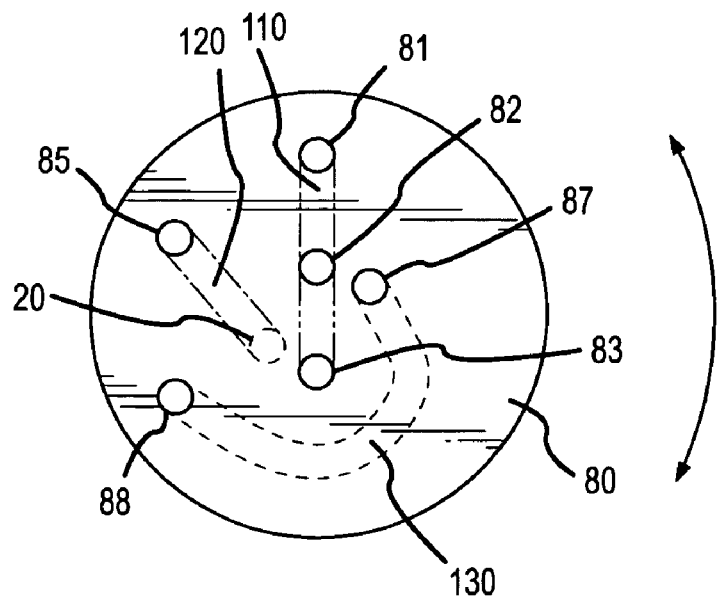
FIG. 4h is a distal view of a manifold of the medical liquid administration apparatus of FIG. 1.

Referring now to FIGS. 4e-4f, which illustrates one embodiment of the valve 30 in an admin position, manifold port 85 may be aligned with abutting seat port 94 when the valve 30 is in an admin position, thereby allowing flow of a medical liquid (e.g., liquid medication) through the second liquid delivery line 60, through the valve 30, catheter interconnection line 50 and to a patient 100. That is, when the valve 30 is in an admin position, a fourth flow path defined by seat port 94, manifold port 85, passageway 120 and manifold port 20 may be established, and this fourth flow path may allow flow of a medical liquid (e.g., liquid medication) through second medical liquid delivery line 60, valve 30, and catheter interconnection line 50. More particularly, liquid medication from liquid medication source 62 may pass through the second medical liquid delivery line 60, through valve 30, catheter interconnection line 50 and, ultimately, to patient 100. To administer liquid medication and with reference to FIG. 2, the liquid medication source 62 may be controlled to infuse the medical liquid into the catheter 112. For example, when liquid medication source 62 comprises a syringe, the plunger 14 may be advanced relative to the barrel thereof to achieve administration. In one approach, the liquid medication source 62 may be mounted in an automated device for automated dispensing of pre-selected dosage amounts. Clip 64 may be manipulated to occlude, or close, second medical liquid delivery line 60 during periods between liquid medication administrations.

Referring back to FIG. 4d, manifold 80 may further include manifold ports 87, 88 and corresponding passageway 130, but neither manifold port 87 nor manifold port 88 may be aligned with any of seat ports 92, 94, 96 in either a prime or flush position. Thus, flow of medical liquids through manifold ports 87, 88 and passageway 130 may not be possible when the valve is in a prime or flush position. However, and as described in further detail below, the valve 30 may be rotated to another position to position manifold ports 87, 88 in relation to seat ports 96, 92 respectively, to allow flow of medical liquids through the apparatus 1.

For example and with reference to FIGS. 4e-4f, which illustrates the valve 30 in an admin position, manifold ports 87, 88 may be aligned with abutting seat ports 96, 92, respectively, when the valve 30 is in an admin position, thereby allowing flow of a medical liquid (e.g., a flush solution) through the first medical liquid delivery line 40 and into the fluid chamber 16. That is, when the valve 30 is in an admin position, a fifth flow path defined by seat port 96, manifold port 87, passageway 130, manifold port 88 and seat port 92, may be established, and this fifth flow path may allow flow of a medical liquid through the first medical liquid delivery line 40 and into the fluid chamber 16. More particularly, the plunger 14 may be retracted relative to the barrel 12 and medical liquid from first medical liquid source 42 may be drawn into fluid chamber 16 via first medical liquid delivery line 40 and this fifth flow path to fill such fluid chamber 16. To administer the flush solution from the fluid chamber 16, valve 30 may be moved (e.g., via a pull and turn action) into the flush position shown in FIGS. 4c-4d. For example and as discussed in further detail below, the user may anchor the barrel 12 of the apparatus 1 with one hand and grasp the valve housing 70 with another hand to pull the valve housing 70 away from the barrel 12 and then rotate the valve housing 70 relative to the barrel 12 to change from one valve position to another valve position. Alternatively, the user may use only one hand to move the valve 30, such as by anchoring the barrel 12 with two or more fingers and pushing and turning the valve housing 70 with a thumb. Thereafter, plunger 14 may be advanced so as to flow the flush solution through a flow path (e.g., via the above-described third flow path) to the catheter interconnection line 50.

As will be appreciated, the above-described fourth flow path (i.e., manifold ports 20, 85 passageway 120 and seat port 94) and fifth flow path (i.e., manifold ports 87, 88, passageway 130 and seat ports 92, 96) may be and generally are fluidly isolated from one another. Thus, when the valve 30 is in an admin position, two separate and isolated flows of medical liquids through the apparatus 1 may be established, such as a flow of a liquid medication to a patient 100 and a flow of a flush solution into the fluid chamber 16 of the syringe-like device 10, and such separate and isolated flows may occur at least concurrently. As discussed in further detail below, these separate but concurrently usable flow paths provide utility in that interconnections between the patient 100 and the apparatus 1 may be maintained through repeated administrations of liquid medication. As will further be appreciated, the above noted third through fifth flow paths may be and generally are fluidly isolated from one another to restrict fluid communication between the various fluids.

Of note and with reference to FIG. 2, it will be appreciated that, prior to the infusion of a liquid medication or flush solution, administration apparatus 1 may be conveniently employed for effective catheter aspiration. In particular, when the valve 30 is in a flush position, the plunger 14 may be retracted to manually draw a small amount of blood through an interconnected catheter 112 and into a tubing line 58 to allow medical personnel to confirm proper catheter placement and/or the absence of an obstruction in the catheter (e.g. blood clotting, bacterial growth, etc.). Then, plunger 14 may be advanced to return the blood.

An exemplary procedure using the medical liquid administration apparatus 1 will now be presented. To begin the procedure, the liquid administration apparatus 1 may be removed from sterile packaging and set-up procedures completed. In particular, and with reference to FIGS. 2 and 4a-4b, valve 30 may be oriented in a prime position, and a flush solution source 42 (e.g., a multi-dose saline or heparin flush solution source, such as a saline or heparin flush solution source comprising at least 50 milliliters of solution) may be fluidly interconnected to port 96 of the medical liquid administration apparatus 1 via first medical liquid delivery line 40. Of note, the distal end of first medical liquid delivery line 40 may be fluidly interconnected to flush solution source 42 and may include a one-way check valve 43, which only allows flow of flush solution through the first medical liquid delivery line 40 toward the valve 30. A proximal end of the second medical liquid delivery line 60 may be fluidly interconnected to port 94 and a distal end of the second medical liquid delivery line 60 may be capped with a cap (not shown). Fluid chamber 16 may be fluidly interconnected to port 92. Upon fluid interconnection of the first medical liquid delivery line 40 to flush solution source 41, the plunger 14 may be retracted to draw a flush solution into fluid chamber 16 from flush source 42 via first medical liquid delivery line 40 and the above-described first flow path. Upon filling fluid chamber 16 with flush solution, the cap located on the distal end of second medical liquid delivery line 60 may be removed. Subsequently, the syringe-like device 10 may be oriented with a distal end of the second medical liquid delivery line 60 being above the fluid chamber 16. Plunger 14 may then be advanced, thereby removing fluid (e.g., air and flush solution) in the fluid chamber 16 and into the second medical liquid delivery line 60 via the above-described second flow path. As will be appreciated, the check valve 43 in the first medical liquid delivery line 40 restricts flow of fluids back through the first medical liquid delivery line 40 and into flush solution source 42.

As will further be appreciated, the cap on the distal end of the second medical liquid delivery line 60 assists in enabling the fluid chamber 16 to draw a medical liquid from the first medical liquid delivery line 40 upon retraction of the plunger. However, it will also be appreciated that, in some instances, the cap may be removed from the distal end of the second medical liquid delivery line 60 and the fluid chamber 16 and second medical liquid delivery line 60 may be filled via a gravity flow.

Tubing line 68 may be primed by manipulation or automated control of liquid medication source 62. After the tubing line 68 and second medical liquid delivery line 60 have been primed, the tubing line 68 and second medical liquid delivery line 60 may be connected via connector(s) 61, 63 to interconnect liquid medication source 62 to valve 30 of the medical liquid administration apparatus 1. As will be appreciated, the liquid medication source 62 may be optionally positioned within an automated infusion device as deemed appropriate by medical personnel. Next, the valve 30 may be moved to a flush position, as illustrated in FIGS. 4c-4d, to fluidly interconnect fluid chamber 16 with catheter interconnection line 50 via the above-described third flow path, and plunger 14 may be advanced to prime catheter interconnection line 50 with flush solution from fluid chamber 16. Next, a catheter 112 may be fluidly interconnected to port 20 of the medical liquid administration apparatus 1 via tubing line 58, connectors 51, 52 and catheter interconnection line 50. At this point, all necessary fluid interconnections have been made to allow for the use of medical liquid administration apparatus 1 on a repeated basis over the course of an extended medication therapy.

As will be appreciated, the above described approach assumes that the catheter 112 and tubing line 58 have previously been primed, and this primed catheter 112 has previously been inserted into the patient 100. It will further be appreciated that the catheter 112 could be primed using the syringe-like device 10 (e.g., by interconnecting the catheter 112 to the catheter interconnection line 50 via tubing 58 and connectors 51, 52, orienting the valve 30 in a flush position, and subsequent advancement of plunger 14 to remove a flush solution in fluid chamber 16 to flow such flush solution through catheter interconnection line 50, connectors 51, 52, tubing line 58 and catheter 112).

Reference is now made to FIGS. 1, 2 and 4c-4f. When medical personnel determine that it is an appropriate time to provide a dose of liquid medication, plunger 14 may then be retracted a sufficient amount to allow medical personnel to visually confirm a blood return into the tubing line 58. Upon such confirmation, plunger 14 may be advanced to push the blood back into the patient 100. In many instances, a predetermined amount of flush solution from the fluid chamber 16 may also be administered to the patient 100 after such confirmation.

Next, medical personnel may move valve 30 to an admin position to fluidly interconnect the second medical liquid delivery line 60 with vascular interconnection line 50 via the above-described fourth flow path (i.e., manifold ports 20, 85, seat port 94 and passageway 120), see FIG. 4f. Concomitantly, clip 64 may be positioned to open the tubing line 68 and a predetermined, desired amount of liquid medication may be passed from liquid medication source 62 into catheter 112 via manipulation or automated control of liquid medication source 62. Concomitantly, plunger 14 may be retracted a desired amount to draw flush solution into fluid chamber 16 from first medical liquid delivery line 40 and flush solution source 42 via the above-described fifth flow path (i.e., manifold ports 87, 88, passageway 130 and seat ports 92, 96). When the desired liquid medication infusion is complete, medical personnel may move the valve 30 to the flush position and plunger 14 may be advanced to further infuse the liquid medication and/or flush solution into the patient. Clip 64 may then be repositioned to occlude tubing line 68.

In accordance with described arrangement, multiple infusions of liquid medication may be completed utilizing medical liquid administration apparatus 1, while maintaining fluid interconnections between the medical liquid administration apparatus 1, flush solution source 42 and liquid medication source 62. As may be appreciated, the maintenance of one or more such interconnections simplifies the overall procedure for medical personnel, results in reduced waste relative to prior techniques, and enhances the maintenance of sterile interconnections.

As noted, the valve 30 may be selectively rotatable about a rotation axis to facilitate selective administration of medical liquids. In this regard and with reference to FIGS. 4b, 4d and 4f, seat ports 92, 94, 96 may be disposed in non-overlapping relation to a rotation axis 35. A non-overlapping spatial relationship between the rotation axis 35 and any seat ports 92, 94, 96 enables these seat ports 92, 94, 96 to selectively communicate with the various manifold ports 81, 82, 83, 85, 87, 88 and corresponding passageways 110, 120, 130. As will be appreciated, if one or more of the seat ports 92, 94, 96 overlapped with the rotation axis 35, it would not be possible to rotate the valve 30 to selectively enable or restrict fluid communication with such overlapping seat ports. Correspondingly, manifold ports 81, 82, 83, 85, 87, 88 may also be-disposed in non-overlapping relation to the rotation axis 35. It will further be appreciated that manifold port 20 may overlap with the rotation axis 35 of the valve. In the illustrated embodiment, manifold port 20 is co-axial with the rotation axis 35 so that the catheter interconnection line 50, which is interconnected to manifold port 20, is not significantly moved during rotation of the valve 30.

As will be appreciated, the seat ports 92, 94, 96 and manifold ports 81, 82, 83, 85, 87 and 88 each include end opening ends and these end openings each include a center axis. One or more of these center axes may be coincidental to the above described barrel axis and/or rotation axis and/or other end opening center axes. Additionally, the first medical liquid delivery may line extend along at least a portion of the barrel about an axis coincidental to one or more of these center axes As will be appreciated, the center axes of the end openings of the ports comprising the first and/or second set of ports may be coincidental with the barrel center axis irrespective of the valve position. That is, irrespective of whether the valve is in a first position (e.g., flush), second position (e.g., admin), third position (e.g., prime) or other valve position, the center axes of the end openings of the ports comprising the first and/or second set of ports may be coincidental with the barrel center axis. In one embodiment, a center axis of a proximal end opening of a port interconnected to a catheter interconnection line may be coincidental and/or co-axial with the rotation axis.

Referring now to FIGS. 1-3b, the fluid interconnections between the valve 30 and medical liquid delivery lines 40, 60 are generally located internally within the syringe-like device 10 and between the proximal end of the valve 30 and the proximal end of the plunger 14, which is advantageous for a variety reasons. By way of illustration, since these fluid interconnections may be within the barrel 12 and/or valve housing 70, the valve 30 and barrel 12 can be coincidentally configured (e.g., both the barrel 12 and valve may be tubular in form). In arrangements where the valve 30 extends proximally away from the proximal end of the barrel 12, the adjacent external surface portions of the valve 30 and barrel 12 may be coincidentally configured. Stated differently, the barrel 12 and valve 30 may define partially overlapping and/or adjacent tubular volumes that are coincidentally shaped and preferably, substantially conformally shaped, and the fluid interconnections between the barrel, the first and second medical liquid delivery lines 40, 60 and/or the catheter interconnection line 50 may be included within such adjacent tubular volumes, such as between the proximal end of the valve 30 and the proximal end of the plunger 14. In this regard, the administration apparatus 1 may be compact and streamlined. That is, since the valve 30 may be tubular in form, it may have a low profile, which may help minimize outside interaction therewith.

Another advantage of the administration apparatus 1 is that many of the various ports and passageways of the valve 30 are not readily observable/hidden. Since many of the various ports and passageways are not readily observable/hidden, awareness of such ports and passageways by a patient, non-medical personnel and others may be decreased, which may reduce undesired manipulation (e.g., by non-medical personnel) of the apparatus 1. Moreover, as the ports and passageways are not readily observable/hidden, the apparatus may appear less complex, which may reduce patient anxiety. As will be appreciated, the aforementioned advantages are by way of illustration only and are not meant to be limiting in any regard.

It will be appreciated that the valve 30 may be assembled in various arrangements to enable flow of medical liquids through the apparatus 1. An exemplary valve assembly is now described with reference to FIGS. 5a-5s.

Figure 5A:
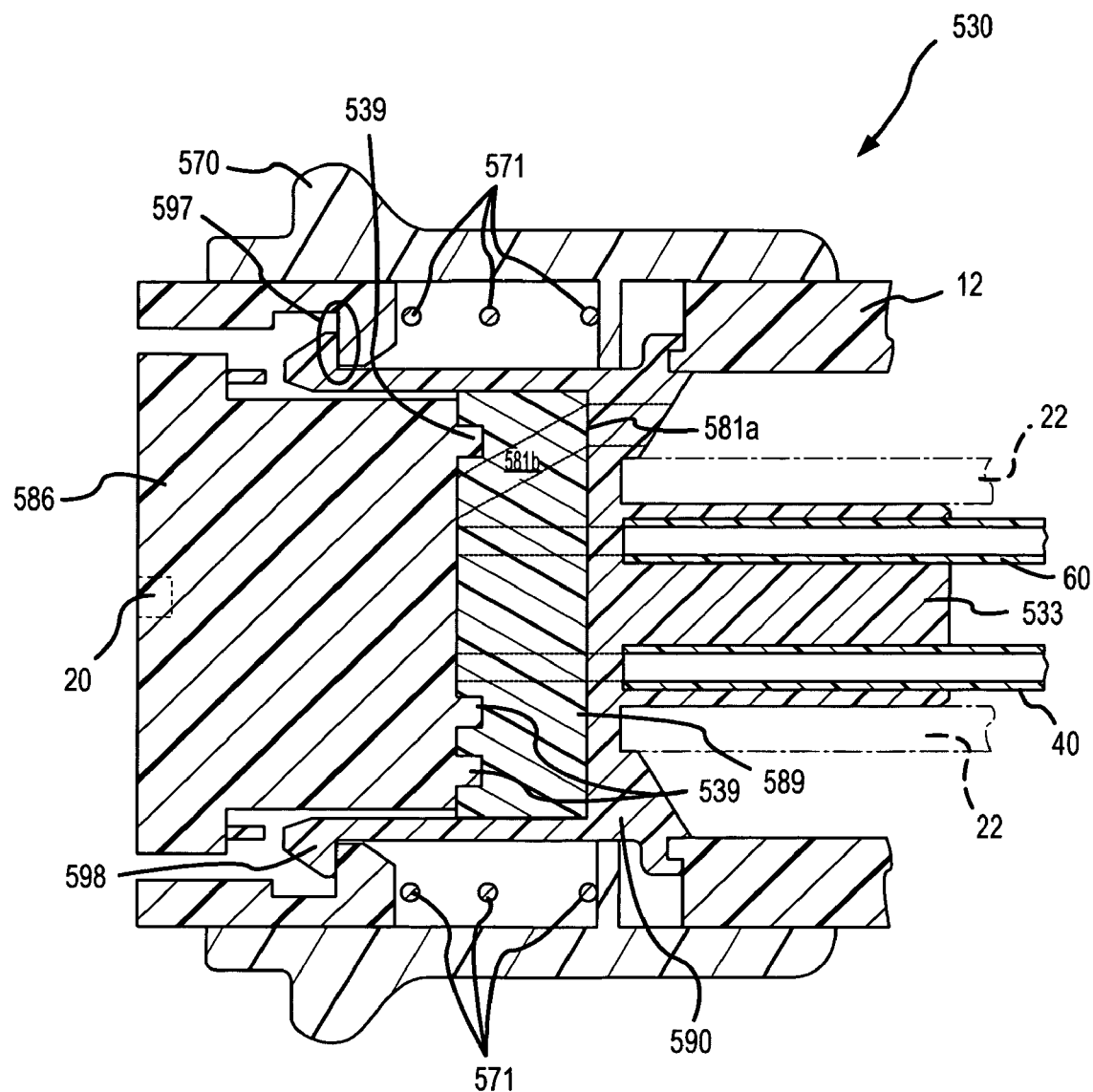
FIG. 5a is a cross-sectional side view of one embodiment of a valve employable in the medical liquid administration apparatus of FIG. 1.

Referring now to FIGS. 5a-5b, the valve 530 generally includes a valve housing 570, a seat 590, and a manifold 580, which includes a rigid portion 586 and an elastomeric gasket portion 589. In the illustrated embodiment, the seat 590 is fixedly interconnected to the barrel 12, and the manifold 580 is interconnected to the seat 590 and movable relative to (e.g., rotatable within and about) the seat 590. The valve housing 570 may be movably interconnected to the barrel 12 and seat 590 and movable in two transverse planes relative to the barrel 12 and seat 590.

Figure 5C:
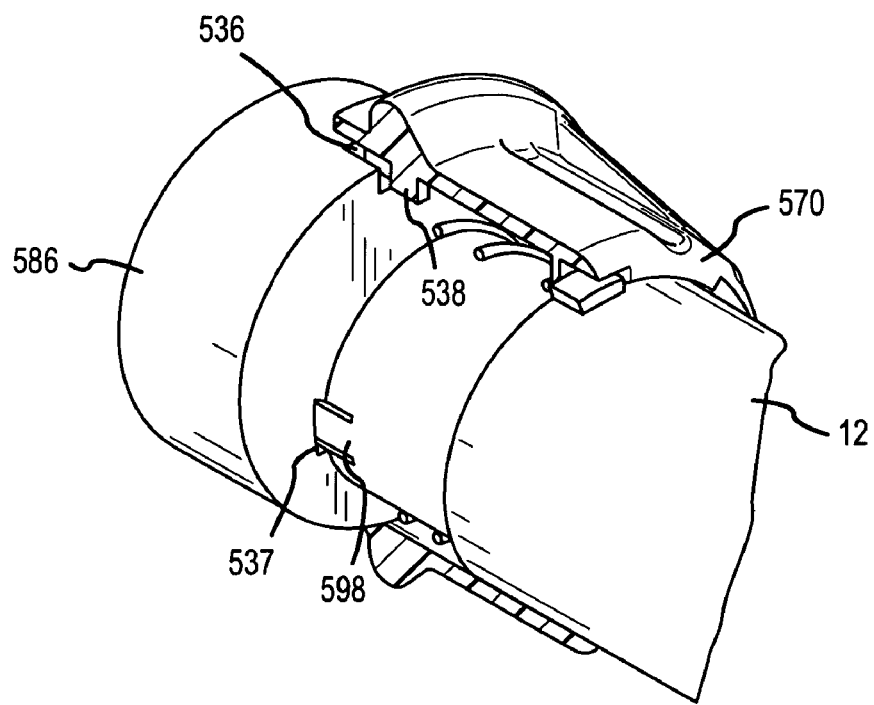
FIG. 5c is a perspective view of the valve embodiment of 5a in one position and having a portion cut away to show internal features.
Figure 5D:
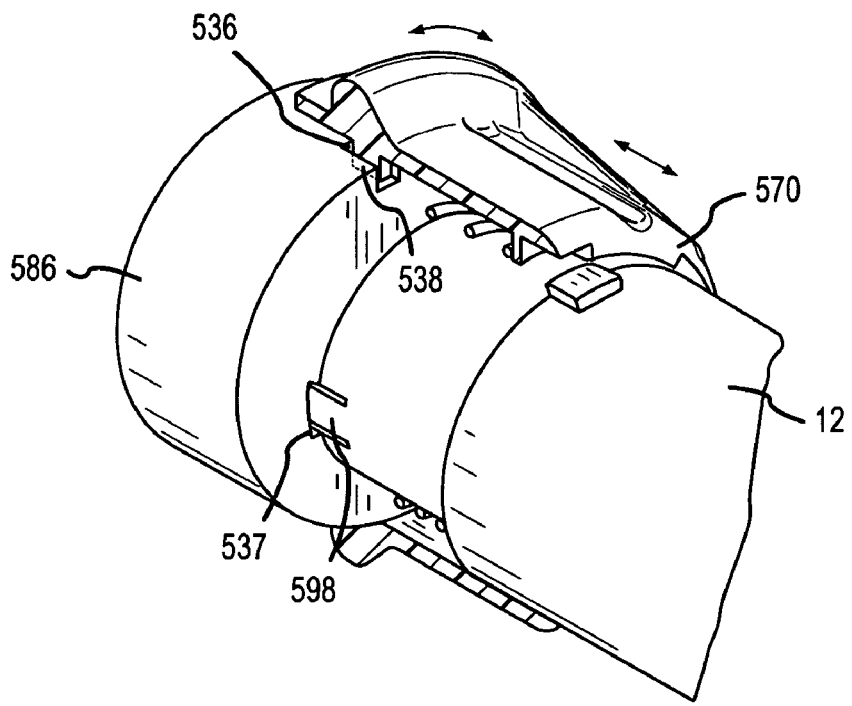
FIG. 5d is a perspective view of the valve embodiment of 5c in another position.
Figure 5E:
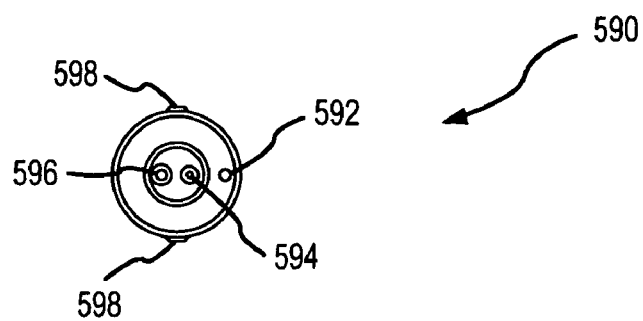
Figure 5F:
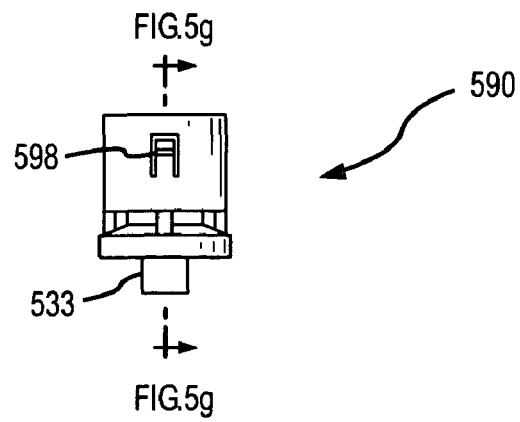
Figure 5G:
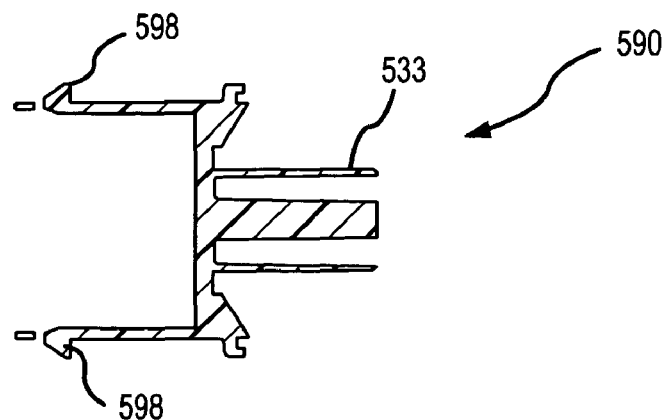
Figure 5H:
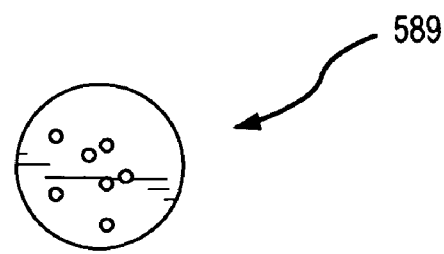
Figure 5I:
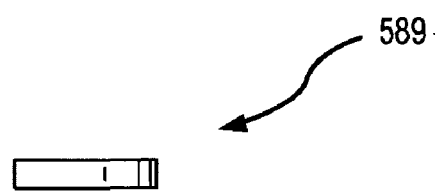
Figure 5J:
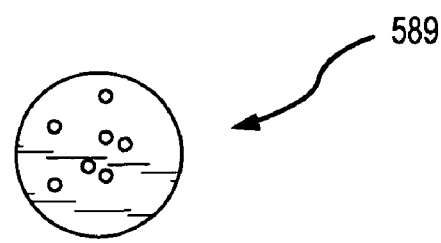
Figure 5K:
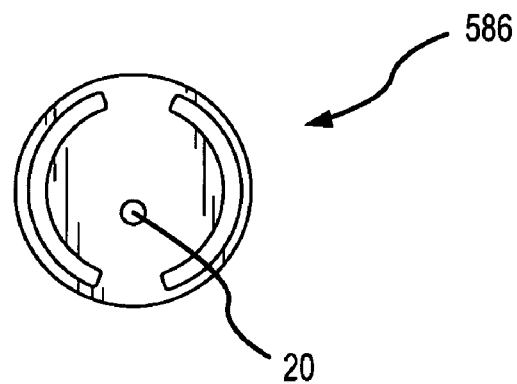
Figure 5L:
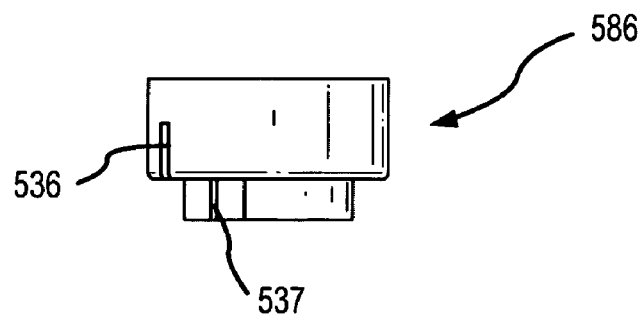
Figure 5M:
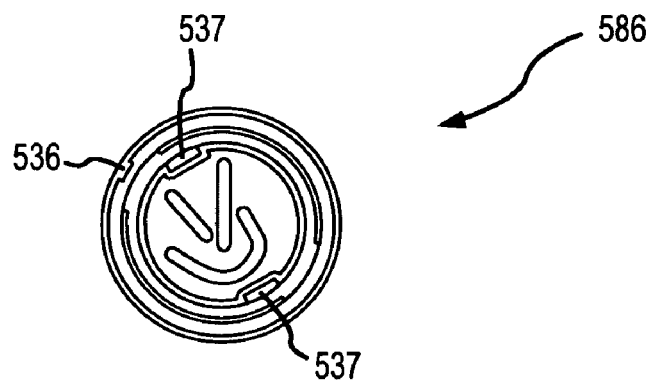
Figure 5N:
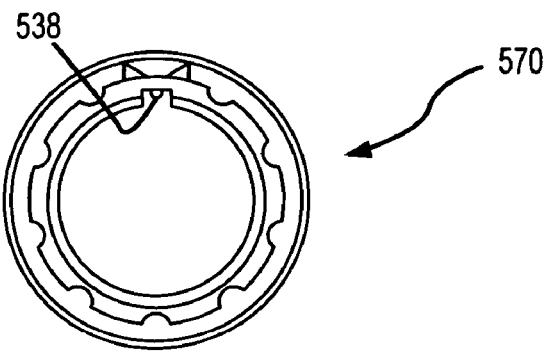
Figure 5O:
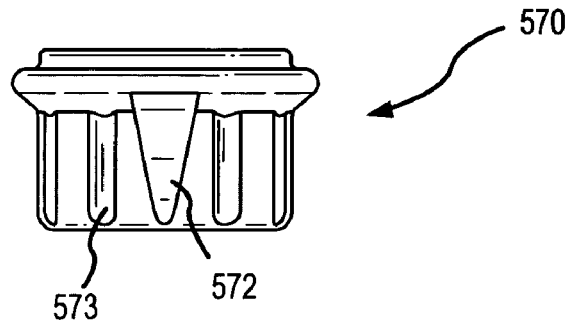
Figure 5P:
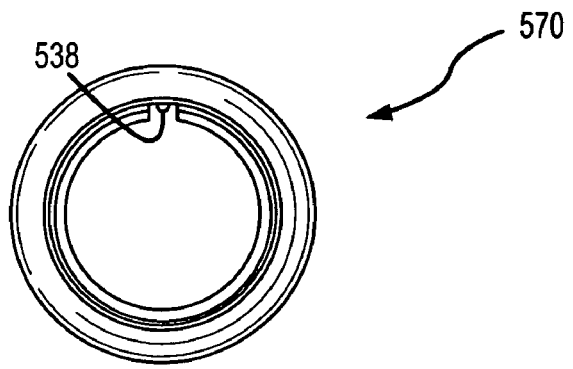

More particularly, the valve housing 570 may be mounted relative to manifold 580 to allow the valve housing 570 to move in an axial (e.g., linear) direction to repeatedly engage and disengage the manifold 580. In this regard and with reference to FIGS. 5c-5d, the manifold 580 may include a receiving path 536 adapted to receive and engage a notch 538 of the valve housing 570. The valve housing 570 may also be mounted relative to the seat 590 and barrel 12 to allow the valve housing 570 to rotate about an axis to correspondingly rotate the manifold 580 when a portion of the receiving path 536 and notch 538 are engaged. As discussed above, the valve 530 may correspondingly be positionable to different positions (e.g., prime, flush and admin positions) to align various ports within the valve 530 to allow selective flow of medical liquids through the apparatus 1.

Referring now to FIGS. 5a, 5b and 5e-5g, the seat 590 may be fixedly interconnected to the barrel 12 and may include a first set of ports 592, 594, 596 fluidly interconnected to the barrel 12, second medical liquid delivery line 60 and first medical liquid delivery line 40, respectively. In the illustrated embodiment, the seat 590 further includes a male portion 533 extending in a distal direction for mating with a proximal end of tubular member 22 and interconnecting with medical liquid delivery lines 40, 60. As will be appreciated, seat ports 594, 596 may be included in this male portion 533. As discussed in further detail below, the seat also includes a flexible hook 598 for engaging a ledge 597 of manifold 580 to secure assembly of valve 530.

Referring now to FIGS. 5a, 5b and 5h-5j, the gasket 589 may be movably interconnected to the seat 590 and fixedly interconnected to the rigid manifold portion 586 via lugs 539. The gasket may comprise an elastomeric material (e.g., a plastic or rubber-based material), which may assist in providing a fluid seal between the seat 590, gasket 589, and rigid manifold portion 586. The gasket 589 may be adapted for rotation within and relative to seat 590 to provide various flow paths through the apparatus 1. As will be appreciated, the gasket 589 may include a plurality of ports and/or passageways adapted to fluidly interconnect with various ports and/or passageways of the rigid manifold portion 586 and/or seat 590. In one embodiment and with reference to FIG. 5a, the gasket may include a port 581a interconnected to an angled passageway 581b to facilitate fluid interconnections within the valve 530.

Referring now to FIGS. 5a, 5b, and 5k-5m, the rigid manifold portion 586 may be movably interconnected to seat 590 via seat hooks 598 and manifold ledge 597. The rigid manifold portion may further include paths 537 for receiving the seat hooks 598. As described in further detail below, the rigid manifold portion 586 may be adapted for movement (e.g., rotation) relative to seat 590 and corresponding seat hooks 598. Rigid manifold portion 586 may also be fixedly interconnected to gasket 589 via lugs 539. Thus, as rigid manifold portion 586 moves, the gasket 589 may also move therewith. As will be appreciated, the rigid manifold portion 586 may include a plurality of ports and/or passageways adapted to fluidly interconnect with various ports and/or passageways of the gasket 589 and/or a catheter interconnection line 50. As will be appreciated, the arrangement of ports and passageways within the valve 530 may be an arrangement of ports and passageways similar to the arrangement described above in reference to FIGS. 4*a*-4*h*.

Referring now to FIGS. 5*a*-5*d* and 5*n*-5*p*, the valve housing 570 may be movably interconnectable to the manifold 580 to engage and move therewith. The valve housing 570 may also be disposed about and movably interconnected to the barrel 12 to enable movement and selective positioning of the valve 530. More particularly, the valve housing 570 may be adapted for linear movement relative to the barrel 12 (e.g., linear advancement or retraction relative to the barrel 12) and for rotational movement about a rotation axis.

Figure 6A:
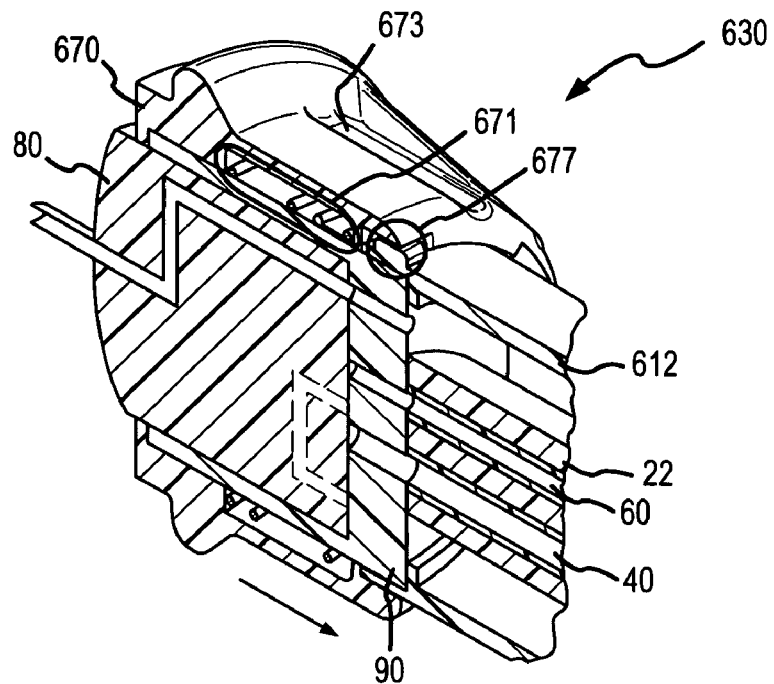
FIG. 6a is a cross-sectional perspective view of various features of the medical liquid administration apparatus.
Figure 6B:
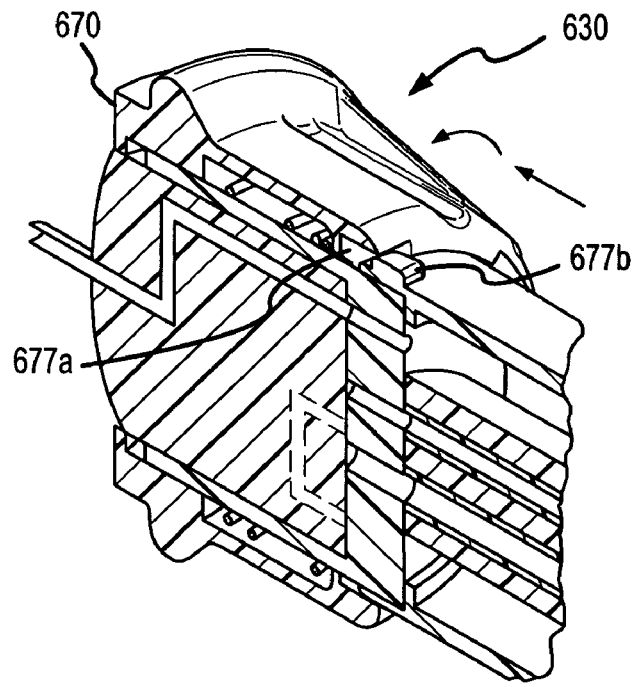
FIG. 6b is a cross-sectional perspective view of various features of the medical liquid administration apparatus.

In this regard, the valve housing may include a notch 538 adapted to sit proximal to and/or in manifold receiving path 536. As valve housing 570 is moved from a first position to a second position, (e.g., linearly advanced in a proximal direction) notch 538 may engage a face of receiving path 536 to correspondingly engage manifold 580. As the valve housing 570 is moved from a second position to a third position (e.g., rotation about an axis), notch 538 may further engage a face of receiving path 536, thereby correspondingly moving manifold 580 with the valve housing 570. As will be appreciated, upon attaining the third valve housing position, valve housing 570 may be moved from a third position to a fourth position (e.g., linearly retracted in a distal direction), which may disengage notch 538 from a face of receiving path 536. In a related embodiment, and as described in further detail below in relation to FIGS. 6*a*-6*b*, a distal portion of the valve housing 570 may include ridges/valleys adapted to engage co-related valleys/ridges on the barrel 12 to restrict the valve 530 from undesirably moving positions. For example, when a ridge is positioned in a portion of a valley, the valve housing 570 may be restricted from rotating.

As will be appreciated, the above described first and fourth valve housing positions may correspond to positions in which the valve housing 570 is engaged with the barrel 12 via such co-related valleys and ridges. As discussed in further detail below in reference to FIGS. 6*a*-6*b*, the valve 530 may also include a biasing member 571 for biasing valve housing 570 in an engaged position with such barrel 12 ridges/valleys. As further described below in relation to FIGS. 7 and 8, the valve housing 570 may also include a sensory indicator 572 for assisting in indicating the position of the valve 530.

A locking system may also be provided to restrict the valve 530 from achieving one or more orientations/positions. As noted above and with reference to FIGS. 1-4*h*, the prime position generally allows the flow of a medical liquid (e.g., a flush solution) through the first medical liquid delivery line 40, through a first flow path to fill fluid chamber 16 to prime such fluid chamber 16. The prime position also allows the flow of a medical liquid from the fluid chamber 16, through a second flow path and into the second medical liquid delivery line 60 to prime such second liquid delivery line 60. After the medical liquid delivery lines 40, 60 and fluid chamber 16 have been primed, the valve 30 may be moved to another position (e.g., a flush position). As will be appreciated, after the priming, it may be unnecessary for the first medical liquid line 40 and/or the fluid chamber 16 to ever liquidly communicate with the second medical liquid delivery line 60. In fact, it could be hazardous to a patient 100 if the second liquid delivery line 60 liquidly communicated with either first liquid delivery line 40 and/or fluid chamber 16 after the medical liquid administration apparatus 1 has been connected to the patient 100, as accidentally deployment of a medical liquid (e.g., liquid medication) may occur. Therefore, a locking system can be employed with the valve 30 to restrict the repositioning of valve 30 after the valve 30 has changed from this shipping position (e.g., after the first occurrence of the prime position).

In this regard and with reference to FIGS. 5*a*, 5*b* and 5*q*-5*s*, the valve 530 may include a locking system or other similar structure designed to restrict the valve 530 from moving to certain orientations/positions. In the illustrated embodiment, the manifold 580 includes manifold ledge 597 fixedly interconnected with catch 599, both of which may be adapted to rotate relative to seat hook 598. The seat hook 598 includes a rounded face and a substantially flat face. As noted above, the seat hook 598 engages the ledge 597 via a bottom face to secure manifold 580 to seat 590. As will be appreciated, an appropriate lubricant (e.g., a silicone-based lubricant) may be used to assist in enabling movement between the seat hook 598 and the ledge 597.

Figure 5Q:
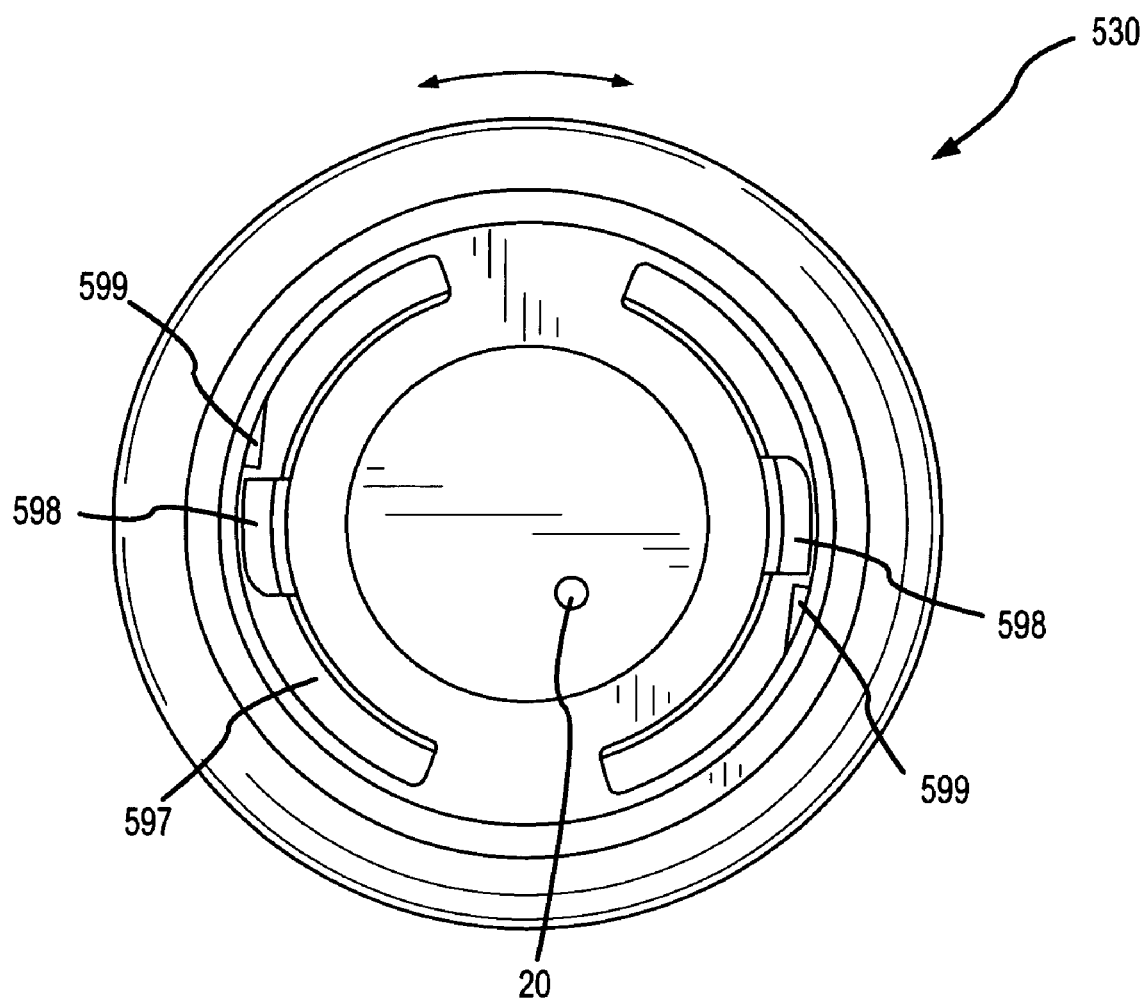
Figure 5R:
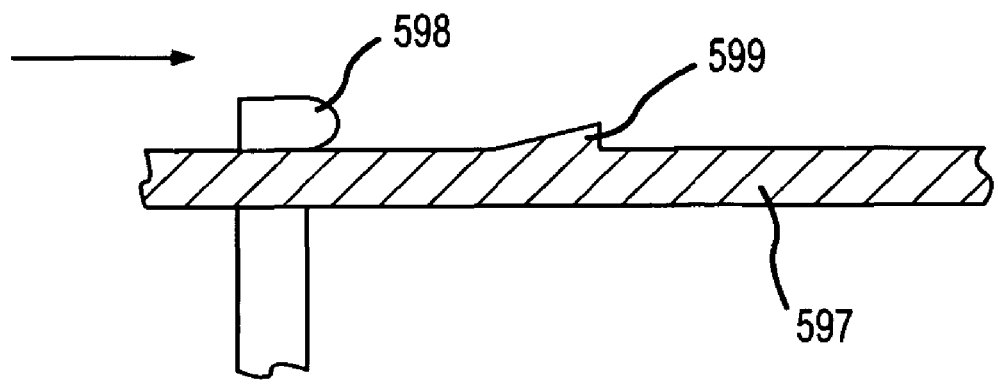
FIG. 5r illustrates a locking system of the valve embodiment of FIG. 5a in a first position.
Figure 5S:
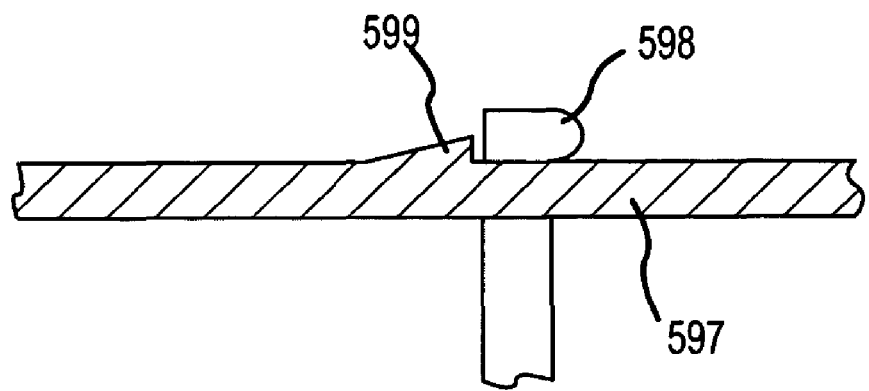
FIG. 5s illustrates a locking system of the valve embodiment of FIG. 5a in a second position.

Referring now to FIGS. 5*q*-5*s*, the medical liquid administration apparatus 1 may be shipped in a shipping position (e.g., a prime position) and moved to another position. As the valve 530 is changed from a shipping/prime position, manifold ledge 597 may move relative to the seat hook 598, and rounded face of the seat hook 598 may engage a ramp portion of the catch 599. Upon movement of the manifold 580 past a certain point, the rounded portion of the seat hook 598 and the ramp portion of the catch 599 may disengage, and the hook 598 may move (e.g., snap) toward a flat face of the catch 599 so that only the flat faces of the hook 598 and catch 599 may physically interact (e.g., abut one another). As will be appreciated, after the manifold 580 is moved past this certain point, the flat faces of the hook 598 and catch 599 may restrict the valve 530 from moving back to the prime position. As will be appreciated, although the locking system has been described in relation to a catch-hook arrangement, any known device/arrangement may be used to restrict the valve 530 from moving to certain orientations/positions. As will further be appreciated, in the illustrated embodiment, flexible seat hook 598 provides dual functionality in that it secures rigid manifold portion 586 to seat and also restricts the valve 530 from achieving certain orientations/positions.

As noted above, a biasing member may be used with the apparatus 1. In one embodiment and with reference to FIGS. 6*a*-6*b*, a valve housing 670 may also include a biasing member 671 adapted to bias the valve housing 670 toward the barrel 612. In this regard, a user may apply a force to the valve housing 670, such as in a proximal direction, to disengage the valve housing 670 from the barrel 612 and engage the valve housing 670 with the manifold 680. Subsequently the valve housing 670 and the manifold 680 may be rotated to move the valve 630 to another position. Thus, one or more components of the valve 630 may be moved in two transverse planes to change between valve positions. That is, various components of the valve 630 may be linearly retracted from the barrel 612, rotated between positions and then advanced relative to the barrel 612 to achieve various valve positions. More particularly, the valve housing 670 may be linearly advanced or retracted along an axis that is coincidental (e.g. substantially parallel to) to a center axis of the barrel 612 and further rotated about an axis that is also coincidental to the center axis of the barrel 612.

In an additional related embodiment, the medical liquid administration apparatus 1 may include components adapted to restrict the valve 630 from moving in at least one of the above referenced two transverse planes. By way of illustration, the valve housing 670 and/or seat 90 and/or barrel 612 may include co-related ridges and valleys adapted to interface with one another to restrict movement of the valve housing 670 in a first plane, and correspondingly the valve 630. In the illustrated embodiment, valve housing 670 includes a ridge/valley arrangement 677, where valve housing valley 677a engages/interfaces with barrel ridge 677b. Such arrangement restricts the valve housing 670 from substantially moving in either a clockwise or counterclockwise direction.

As will be appreciated, the above mentioned biasing member aspects and ridge/valley arrangement may be combined to restrict movement of the valve in both of the above referenced two transverse planes. In this regard and with further reference to FIGS. 6a-6b, the valve 630 may include the biasing member 671 to bias the valve housing 670 in a distal direction (i.e., restrict movement of the valve in a first plane). In one valve position (e.g., a flush position), the valve housing valley 677a and the barrel ridge 677b may be engaged/interfaced to restrict movement of the valve housing 670 (i.e., restrict movement of the valve in another plane transverse to the first plane). As desired, a user may apply a force to the valve housing 670, such as in a proximal direction, to disengage/separate the valve housing valley 677a from the barrel ridge 677b. Correspondingly, the user may move the valve housing 670 (e.g., rotate the valve housing 670 in a clockwise or counterclockwise direction) to another position (e.g., an admin position). Subsequently, the user force may be removed and the biasing member 671 may bias the valve housing 670 in a distal direction.

In a further related embodiment, a second ridge/valley arrangement may be provided to help properly position the valve housing 670 in relation to the seat 90 and/or the barrel 612, and consequently help properly position the manifold 680 in relation to the seat 90. For example, the valve housing 670 may include one valley (e.g., 677a) and the barrel 612 may include a plurality of barrel ridges (e.g., 677b, 677c). When the valve 630 is in a flush position, the valve housing valley 677a engages/interfaces with a first barrel ridge 677b. When the valve position is changed (e.g., via pulling/pushing and/or rotating the valve housing 670), but is not yet in the above described another position (e.g. an admin position), ridge portions of the valve housing 670 (e.g., non-valley portions) may interface with ridge portions of the barrel 612, thereby restricting the valve housing 670 from reengaging the barrel 612. When the valve 630 attains the desired another position, the valve housing valley 677a may align with second barrel ridge 677c (not shown) thereby enabling the valve housing 670 to reengage the barrel 612. As will be appreciated, this approach is useful in conjunction with the above-described biasing member approach to help provide confirmation that the valve 630 is in a correct orientation.

In a further related embodiment, the valve housing 670 may also be adapted to facilitate user grip of the valve 630, such as by providing, on an external surface of the valve housing 670, an abrasive material, dimples, valleys or other material/structure adapted to facilitate user movement of the valve 630. In the illustrated embodiment of FIGS. 6a-6b, the valve housing 670 contains valleys 673 adapted to facilitate user grip and movement of the valve 630.

In another approach and with reference back to FIG. 1, the medical liquid administration apparatus 1 may be provided with a sensory indicator system to indicate the alternate positionability of the valve 30. For example, the valve 30 may include a first visual indicator, such as observable markings (e.g., an arrow), and the syringe-like device 10 may include a set of second visual indicators corresponding to the orientation of the valve 30. The set of second visual indicators may be various different words/characters located at various different positions on the syringe-like device 10, each second indicator indicating to a user in which position the valve 30 is located relative to fluid chamber 16 and/or medical liquid delivery lines 40, 60. That is, the visual indicators may indicate where the valve 30 needs to be positioned to achieve a given mode of operation and may further indicate which given mode of operation the valve 30 is currently positioned to perform. By way of example, the set of second visual indicators may be three different words located at three different positions on the barrel 12, each second visual indicator indicating whether the valve 30 is in a prime, flush and admin position, respectively.

Figure 7A:
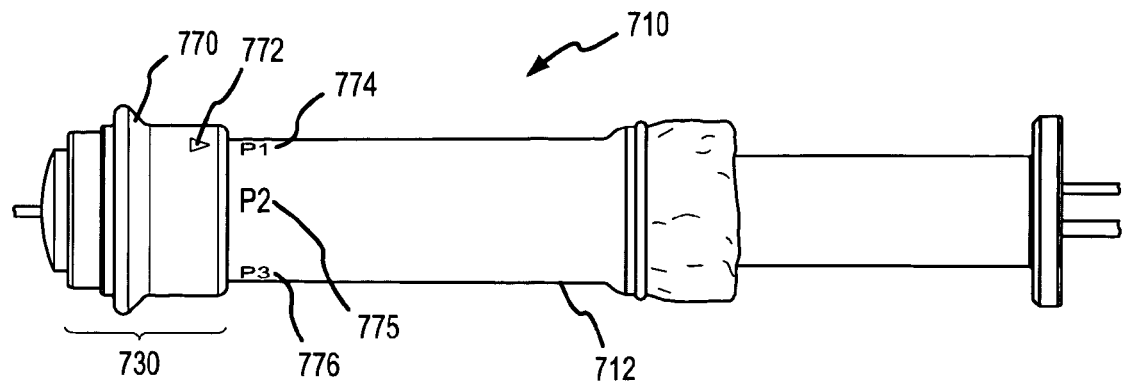
FIG. 7a is a perspective side view of one embodiment of a sensory indicator system of the medical liquid administration apparatus in a first position.
Figure 7B:
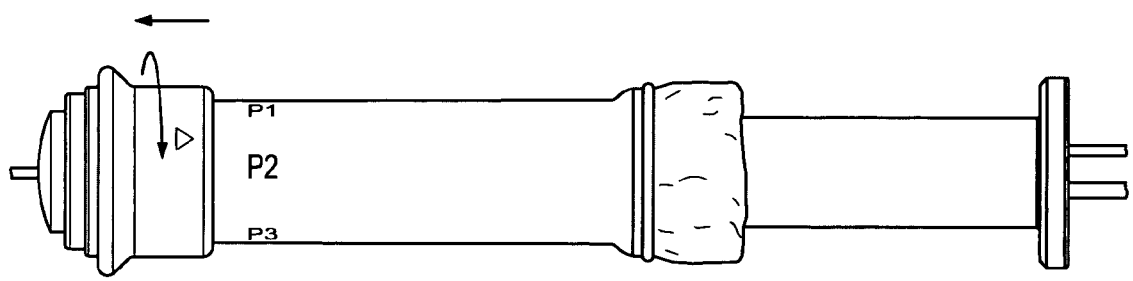
Figure 7C:
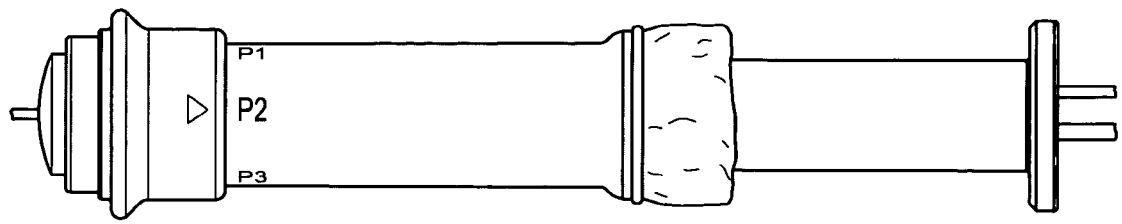
FIG. 7c is a perspective side view of the sensory indicator system of FIG. 7a in a second position.

One embodiment of a sensory indicator system is illustrated in FIGS. 7a-7c. A valve housing 770 includes a valve housing visual indicator 772 and the syringe-like device 710 includes a set of barrel visual indicators 774, 775, 776. When the valve 730 is in a first position, the valve housing visual indicator 772 may be oriented in relation to barrel visual indicator 774 (e.g., substantially in line with) so that a user is aware that the valve 730 is oriented in such first position. Correspondingly, when the valve 730 is in a second position, the valve housing visual indicator 772 may be oriented in relation to barrel visual indicator 775, and when the valve 730 is in a third position, the valve housing visual indicator 772 may be oriented in relation to barrel visual indicator 776. Further, the user may be aware as to the alternate positionability of the valve 730 to other positions via a non-aligned relationship (e.g., a non-linear relationship) between the valve housing indicator 772 and any one of the barrel visual indicators 774, 775, 776.

Figure 8:
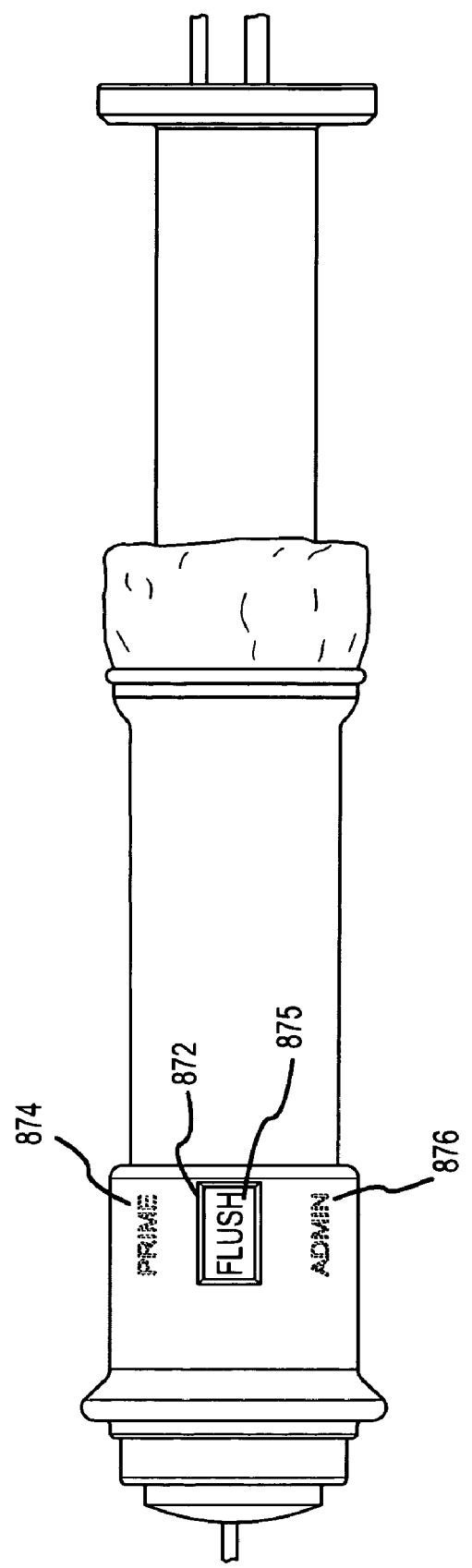
FIG. 8 is a perspective side view of one embodiment of a sensory indicator system of the medical liquid administration apparatus.

In another embodiment and with reference to FIG. 8, the sensory indicator system may include a window 872 as a first visual indicator, the window 872 being adapted to display one visual indicator from a set of second visual indicators 874, 875, 876, each one of the set of second visual indicators corresponding to a position of the valve 830. For example, the window 872 may be adapted to display only one of a prime position indicator 874, flush position indicator 875, and admin position indicator 876 at a time. As will be appreciated, restricting the indication of the positionability of the valve to a single visual indicator may tend to reduce undesired manipulation (e.g., non-medical personnel) of the apparatus.

As will be appreciated, any of the above-described sensory indicator aspects, biasing member aspects and ridge/valley arrangement may be combined. In this regard and referring back to FIGS. 6a-6b, the valve housing 670 may be moved in a first direction (e.g., pulled away from the barrel 612) to disengage a valley 677a on the valve housing 670 from a corresponding ridge 677b on the barrel 612 or seat 90. Subsequently, the valve housing 670 may be rotated from a first position to a second position using the first visual indicator and set of second visual indicators as a guide. Upon attaining the desired second position, the valve housing 670 may be moved (e.g., via a biasing member) in a second direction (e.g., toward the barrel 612) and a valve housing ridge/valley may engage a valley/ridge on barrel 612 or seat 90.

Figure 9:
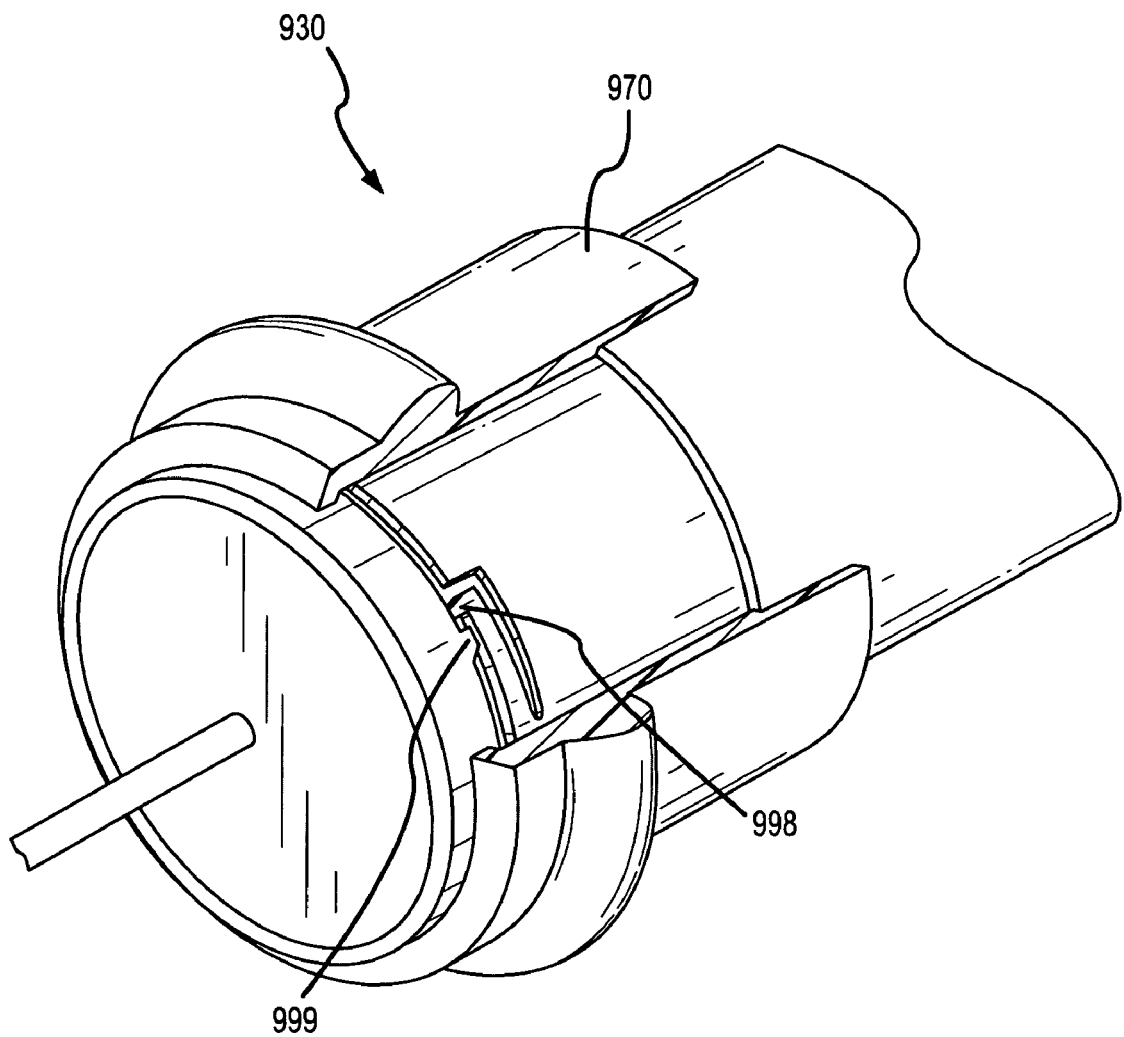
FIG. 9 is a perspective cut-away view of one embodiment of a locking system of the medical liquid administration apparatus.

As noted above, a locking system may be provided to restrict the valve 30 from achieving certain orientations/positions. Another embodiment of a locking system is now described in reference to FIG. 9. The locking system may include a hook and catch arrangement, the hook 998 including ramp and flat portions and the catch 999 also including ramp and flat portions. When the 930 valve is changed from a prime position, the ramps from each of the catch 999 and hook 998 may be arranged such that they may physically interact, such as by sliding past one another, so that the valve housing 970 can be rotated to another position (e.g., a flush or admin position). Upon rotation of the valve housing 970 past a certain point, the ramps may disengage and the hook 998 may move (e.g., snap) toward the proximal end of the valve housing 970 so that only the flat portions of the hook 998 and catch 999 may physically interact (e.g., abut one another). As will be appreciated, after the valve housing 970 is moved past this certain point, the flat portions of the hook 998 and catch 999 restrict the valve housing 970 from moving back to the prime position. Thus, valve 930 may be restricted from returning to the prime position using a locking system. As will be appreciated, although the locking system has been described in relation to a catch-hook arrangement, any known device/arrangement may be used to restrict the valve 930 from moving to certain orientations/positions.

As will be appreciated, the above-described sensory indicator system aspects and locking system aspects of the medical liquid administration apparatus 1 may also be combined. For example and with reference to FIGS. 8 and 9, a sensory indicator system may include a window (e.g., window 872) and corresponding set of visual indicators (e.g., visual indicators 874, 875, 876). In a prime position, the sensory indicator system and may indicate that the valve 830 is in the prime position, via window 872 aligned with prime position indicator 874. Upon movement of the valve 830 to another position (e.g., a flush position), the prime position indicator 874 may be hidden from view. Correspondingly, a locking system may be used to restrict the valve 830 from being returned to the prime position (i.e., after the first occurrence of the prime position, the valve 30 may be restricted from visually indicating the existence of the prime position). Thus, undesired manipulation of the apparatus 1 may be further reduced.

Figure 10:
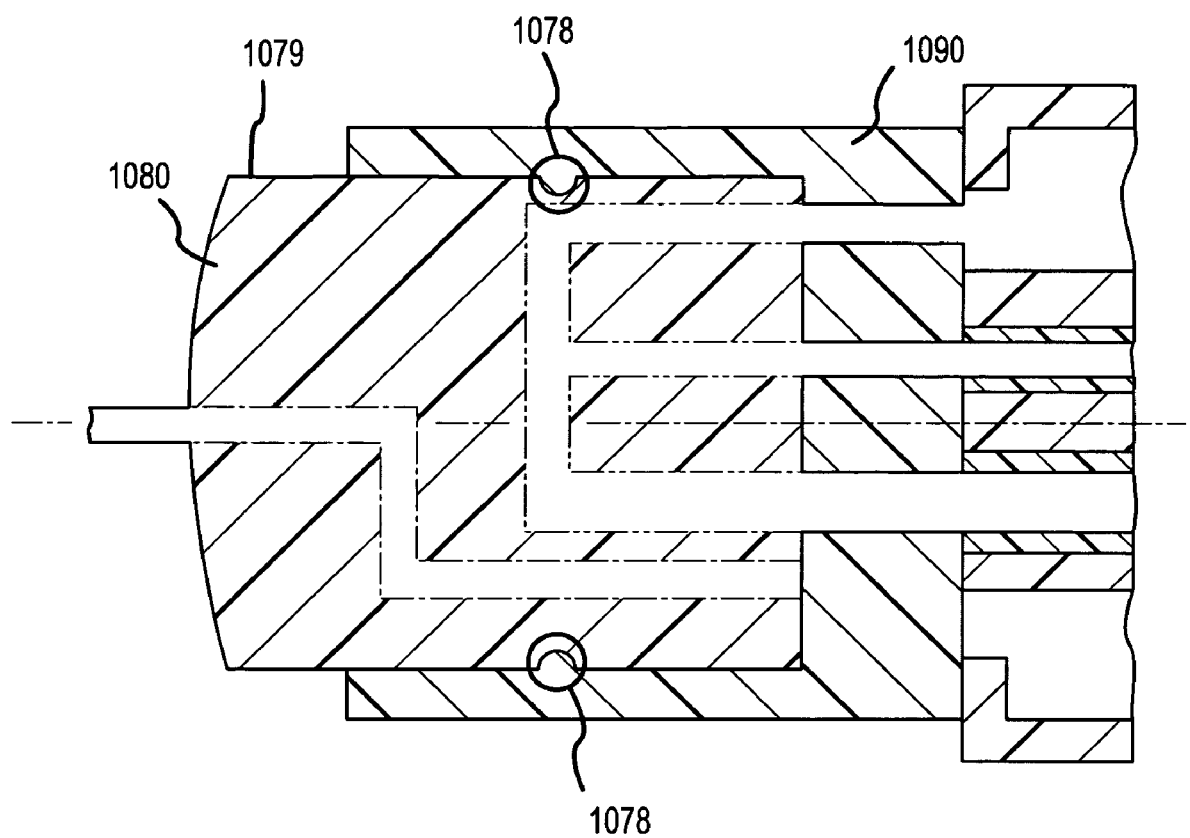
FIG. 10 is a cross-sectional side view of one embodiment of a valve of the medical liquid administration apparatus.

As described in relation to FIGS. 1-2, the valve 30 includes a valve housing 70. It will also be appreciated that the valve 30 may be used without a valve housing 70. For example and as depicted in FIG. 10, a manifold 1080 may be interconnected with a seat 1090 such that the manifold 1080 may be held in place by a ridge/valley arrangement 1078. The outer protruding portion of the manifold 1079 may include an abrasive material, dimples, valley or other material/structure adapted to facilitate user movement of the manifold 1080.

As described above, the valve 30 may be fixedly interconnected to the proximal end of the barrel 12 and extend therefrom. However, it will be appreciated that the valve 30 may be integrally defined by a portion of said barrel 12 and/or the valve 30 may be disposed at least partially within a portion of the barrel 12. In this regard, it will be appreciated that the seat 90 may be fixedly interconnected to or within a proximal end of the barrel 12.

Referring back to FIG. 3a, it will be appreciated that the medical liquid delivery lines 40, 60 may be interconnected to the valve 30 in various orientations. As noted above, to facilitate interconnection of the lines 40, 60 to the valve 30, the tubular member 22 may be disposed within barrel 12 and fixedly interconnected to seat 90 to facilitate interconnection of the medical liquid delivery lines 40, 60 to valve 30. In this regard, the tubular member 22 may include apertures located at the proximal and/or distal ends thereof for receiving medical liquid delivery lines 40, 60 and interconnecting with the valve 30. Further in this regard, the tubular member 22 may include at least one passageway for interconnecting the apertures. As illustrated, the medical liquid delivery lines 40, 60 interconnect with valve 30 through apertures and passageways of the tubular member 22 and plunger 14. As noted above, placement of the medical fluid delivery lines 40, 60 within at least a portion of the syringe-like device 10 creates a streamlined, compact and low profile apparatus. As will be appreciated, the medical liquid delivery lines 40, 60 may extend substantially linearly through the syringe-like device 10, as depicted in FIG. 3a, or non-linearly, such as in a coiled orientation.

Figure 11:
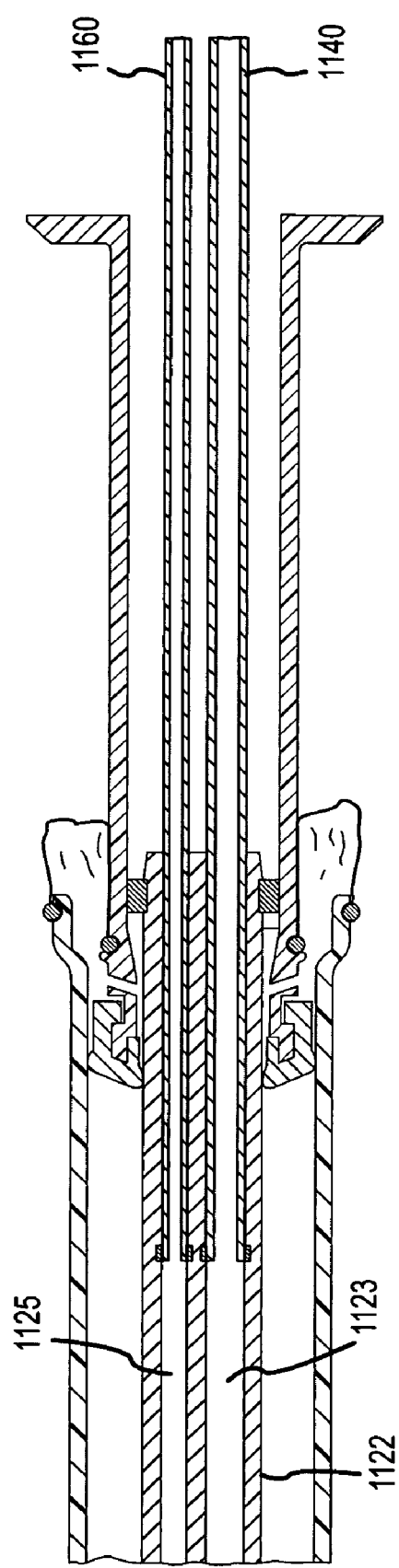
FIG. 11 is a cross-sectional side view of one embodiment of the interconnection between medical liquid delivery lines and a tubular member.
Figure 12:
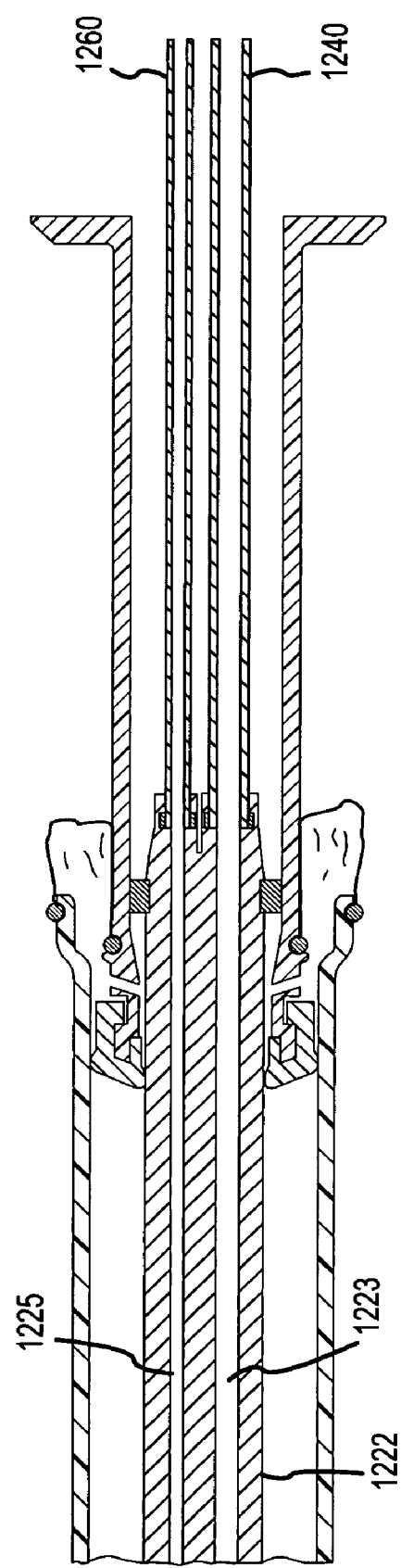
FIG. 12 is a cross-sectional side view of one embodiment of the interconnection between medical liquid lines and a tubular member.

In an alternative embodiment and with reference to FIG. 11, medical liquid delivery lines 1140, 1160 may extend only through a portion of passageways 1123, 1125 of tubular member 1122 to interconnect therewith and the remaining portion of the passageways 1123, 1125 may fluidly interconnect the medical liquid delivery lines 1140, 1160 to the valve. In another embodiment and as illustrated in FIG. 12, medical liquid delivery lines 1240, 1260 may extend to and interconnect with the distal end of tubular member passageways 1223, 1225, with the majority of the tubular member passageway 1223, 1225 being used to fluidly interconnect the medical liquid delivery lines 1240, 1260 to the valve.

Figure 13:
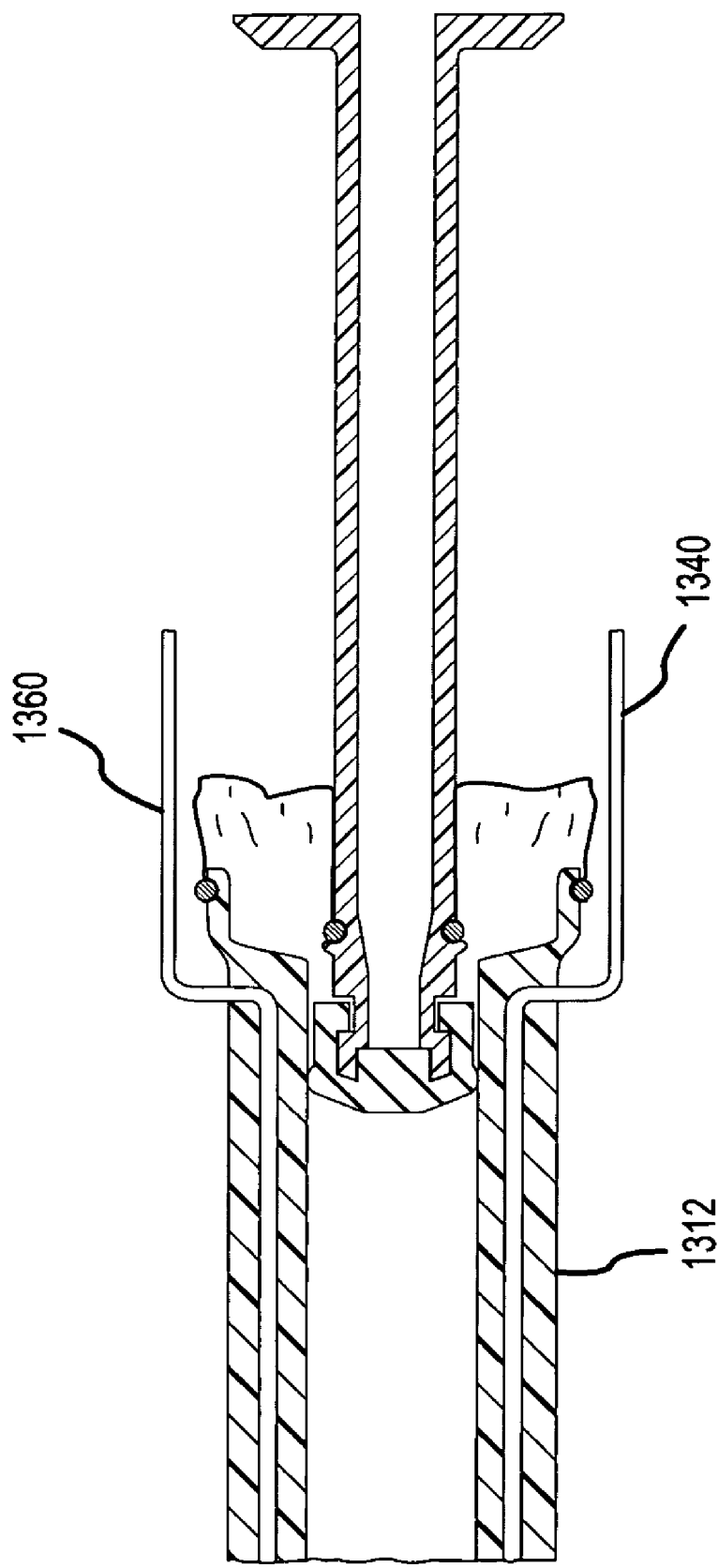
FIG. 13 is a cross-sectional side view of one embodiment of medical liquid lines disposed within a sidewall of a barrel.

In another approach, the tubular member may be excluded from the apparatus 1 and the medical liquid delivery lines may be interconnected to the valve in another manner. For example and with reference to FIG. 13, the medical liquid delivery lines 1340, 1360 may extend through a sidewall of the barrel 1312 to interconnect with the valve.

Figure 14:
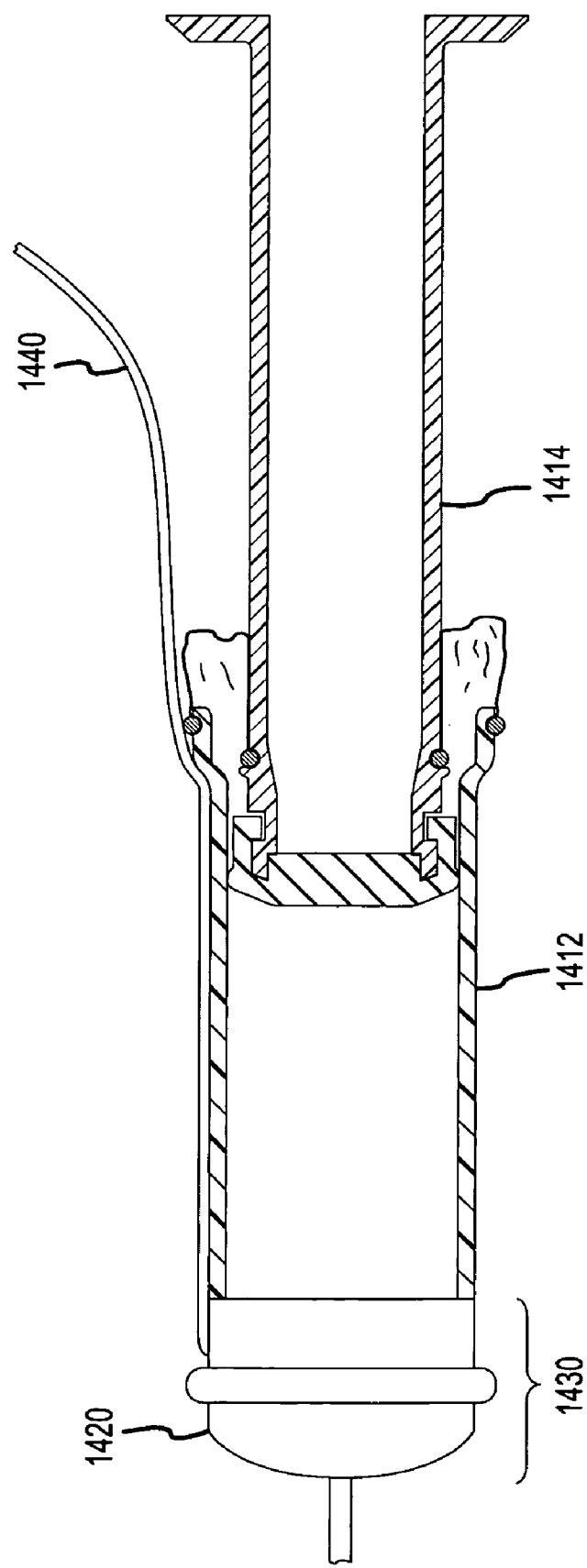
FIG. 14 is a cross-sectional side view of one embodiment of a medical liquid line interconnected to the valve.

In an alternate embodiment and with reference to FIG. 14, a medical liquid delivery line 1440 may interconnect to the valve 1430 through the valve housing 1470. In this regard, the medical liquid delivery line 1440 may be disposed on and extend along the outside of barrel 1412 and plunger 1414 and enter valve 1430 at valve housing 1470 to interconnect therewith.

As will be appreciated, the above described approaches, aspects and embodiments have been described in relation to placement of the valve, valve housing, manifold, seat, biasing member, sensory indicator system, ridge/valley arrangement, locking system and other components in relation to the proximal end of the syringe-like device. However, it will be appreciated that such approaches, aspects and embodiments are illustrative, and that various ones of these components may be placed in relation to the middle of the syringe-like device (e.g., placing the manifold within the tubular member and the valve housing on an external portion of the middle of the barrel), and/or in relation to the distal end of the syringe-like device (e.g., placing the valve housing on a distal end of the barrel), and/or in relation to the plunger (e.g., placing the manifold within the plunger housing and the valve housing on an external surface of the plunger), and such arrangements are expressly contemplated and included within the present invention.

As will further be appreciated, while the apparatus has been described in relation to the use of two medical liquid delivery lines, more than two medical liquid delivery lines could be utilized. By way of illustration, a third medical liquid delivery line may be utilized to deliver a third medical liquid (e.g. a heparin solution or a second liquid medication) to a patient. Further in this regard, the valve may include any arrangement of ports and passageways to effect administration of the medical liquid from the third medical liquid delivery line. More particularly, the valve may include an arrangement of ports and passageways that enables the valve to be selectively positionable in a fourth, a fifth or more valve positions. By way of primary example, a third medical liquid delivery line may be adapted to administer a heparin solution and the valve may include a fourth valve position to enable the heparin solution to fill the barrel. By way of secondary example, a third medical liquid delivery line may be adapted to deliver a second liquid medication and the valve may include fourth and fifth valve positions, where the fourth valve position allows flow of a flush solution through the valve and to a patient, and a fifth valve position allows flow of a second liquid medication through the valve and to a patient. In the latter example, it will be appreciated that successive flushes may be utilized between administration of a first liquid medication via a second medical liquid delivery line and a second liquid medication via the third medical liquid delivery line. As will further be appreciated, any additional medial liquid delivery line(s) may be interconnected to the valve in any manner described above in relation to the first and second medical liquid delivery lines.

It will further be appreciated that while the apparatus has been described in terms of first through fifth flow paths, such terminology is not meant to be limiting in any manner. A number of flow paths may be utilized to effect operation of the apparatus. Moreover, such numerical flow path notations are not meant to imply any mode or order of operation of the apparatus. Additionally, it will be appreciated that a variety of passageway and port arrangements may be utilized to enable selective fluid flow through valve and thus the administration apparatus. Furthermore, it will be appreciated that while the above-described apparatus was illustrated and described in relation to a vascular catheter, the use of the apparatus with other types of catheters is also expressly contemplated (e.g., with urinary catheters).

Moreover, the embodiments described above are for exemplary purposes only and is not intended to limit the scope of the present invention. Various adaptations, modifications and extensions of the described system/method will be apparent to those skilled in the art and are intended to be within the scope of the invention as defined by the claims that follow.

What is claimed:

1. An apparatus for medical liquid administration comprising:
   a barrel having a proximal end and a distal end;
   a plunger slidably disposed within said barrel and extending from said distal end thereof; and
   a first medical liquid delivery line extending through at least a portion of said plunger and having a proximal end fixedly positioned relative to said barrel, wherein said first medical liquid delivery line is fluidly interconnectable to said barrel proximal to said plunger, and wherein the first medical liquid delivery line extends along at least a portion of the barrel and in a direction distally away from said distal end thereof.

2. The apparatus of claim 1, wherein said first medical liquid delivery line extends through said plunger from a proximal end to a distal end thereof.

3. The apparatus of claim 1, further comprising:
   at least a second medical liquid delivery line having a proximal end fixedly positioned relative to said barrel and extending in a direction distally away from said distal end thereof.

4. The apparatus of claim 3, further comprising:
   a tubular member having at least a portion fixedly positioned within said barrel, wherein said plunger is slidably disposed on said tubular member.

5. The apparatus of claim 4, wherein each said first and second medical liquid delivery lines extends through at least a portion of said tubular member.

6. The apparatus of claim 5, wherein each of said first and second medical liquid delivery lines extends through said tubular member from a proximal end to a distal end thereof.

7. The apparatus of claim 1, further comprising:
   a valve interconnected to said barrel, said valve comprising:
   a plurality of valve ports, wherein a first valve port is fluidly interconnectable to said barrel and a second valve port is fluidly interconnectable to said proximal end of said first medical liquid delivery line.

8. The apparatus of claim 7, wherein in a first valve position said first valve port is fluidly interconnected to said barrel.

9. The apparatus of claim 8, wherein is a second valve position, said second valve port is fluidly interconnected to said proximal end of said first medical liquid delivery line.

10. The apparatus of claim 9, further comprising:
    at least a second medical liquid delivery line having a proximal end fixedly positioned relative to said barrel and extending in a direction distally away from said proximal end of said barrel, wherein in said second valve position said first valve port is fluidly interconnected to said proximal end of said second medical fluid delivery line.

11. The apparatus of claim 10, wherein said valve further comprises:
    a third valve port fluidly interconnected to said second valve port and being fluidly interconnectable to said barrel.

12. The apparatus of claim 11, wherein in said second position, said third valve port is fluidly interconnected to said barrel.

13. The apparatus of claim 1, further comprising:
    a valve fluidly interconnectable to said barrel, wherein said valve is positionable in a plurality of valve positions; and
    a catheter line fluidly interconnected to said valve, wherein in a first valve position a first flow path fluidly interconnects said barrel and said catheter interconnection line.

14. The apparatus of claim 13, further comprising:
    at least a second medical liquid delivery line having a proximal end fixedly positioned relative to said barrel and extending in a direction distally away from said proximal end of said barrel; wherein in a second valve position a second flow path fluidly interconnects said second medical liquid delivery line and said catheter interconnection line.

15. The apparatus of claim 14, further comprising:
    a visual indicator for providing a visual indication of the alternate positionability of said valve in said first valve position and said second valve position.

16. The apparatus of claim 14, wherein said first flow path and said second flow path partially overlap.

17. The apparatus of claim 14, wherein in a third valve position a third flow path fluidly interconnects said barrel, said first medical liquid delivery line and said second medical liquid delivery line.

18. The apparatus of claim 17, wherein said valve is not positionable in said third valve position after a first occurrence of such positioning.

19. The apparatus of claim 17, further comprising:
    a visual indicator for providing a visual indication of said valve in said first valve position, said second valve position, and said third valve position.

20. The apparatus of claim 19, wherein said visual indicator does not provide a visual indication of the positionability of the valve in the third valve position after a first occurrence of such positioning.

21. The apparatus of claim 14, wherein said valve comprises:
at least one component adapted for sequential movement relative to said barrel in two transverse planes for positioning said valve between said first and second valve positions.

22. The apparatus of claim 21, wherein said component is adapted for sequential linear movement and rotational movement relative to said barrel for positioning said valve between said first and second valve positions.

23. The apparatus of claim 21, further comprising:
a biasing member for biasing said component of said valve in a direction coincidental with one of said two transverse planes.

24. The apparatus of claim 13, wherein said valve is interconnected to said proximal end of said barrel and said catheter interconnection line extends proximally away from said valve.

25. The apparatus of claim 1 further comprising:
a valve fluidly interconnectable to said barrel, wherein said valve comprises:
a first set of ports fixed relative to said barrel; and
a second set of ports moveable relative to said first set of ports.

26. The apparatus of claim 25, wherein said first set of ports comprises:
a first port fluidly interconnected to said barrel; and
a second port fluidly interconnected to said first medical liquid delivery line.

27. The apparatus of claim 26, wherein said second set of ports comprises:
a first port fluidly interconnectable to said first port of said first set of ports; and
a second port fluidly interconnectable to said second port of said first set of ports.

28. The apparatus of claim 27, further comprising:
a second medical liquid delivery line having a proximal end fixedly positioned relative to said barrel and extending in a direction distally away from said distal end thereof;
wherein said first set of ports comprises:
a third port fluidly interconnected to said second medical liquid delivery line.

29. The apparatus of claim 28, wherein said second set of ports comprises:
a third port fluidly interconnected to a catheter interconnection line, wherein said catheter interconnection line extends in a direction proximally away from said proximal end of said barrel.

30. The apparatus of claim 29, wherein said third port of said second set of ports is fluidly interconnected to said first port of said first set of ports in a first valve position, and wherein said third port of said second set of ports is fluidly interconnected to said third port of said first set of ports in a second valve position.

31. The apparatus of claim 30, wherein said first and second ports of said second set of ports are fluidly interconnected to said first and second ports of said first set of ports, respectively, in said second valve position.

32. The apparatus of claim 31, wherein said first and second ports of said second set of ports are fluidly interconnected.

33. The apparatus of claim 25, wherein said valve further comprises:
a seat; and
a manifold;
wherein one of said first set of ports and said second set of ports is disposed within said seat.

34. The apparatus of claim 33, wherein said seat is fixedly interconnected to said barrel, wherein said manifold is moveable relative to said seat, and wherein said first set of ports is disposed within said seat and wherein said second set of ports is disposed within said manifold.

35. The apparatus of claim 25, wherein the ports comprising the first set of ports comprises an end opening, and wherein each of said end openings comprises a center axis coincidental to a center axis of said barrel.

36. The apparatus of claim 35, wherein said first medical liquid delivery line extends along at least a portion of said barrel about an axis coincidental to said center axes of said end openings of said ports of said first set of ports.

37. The apparatus of claim 35, wherein one of the ports of the second set of ports comprises a proximal end opening interconnected to a catheter interconnection line, and wherein a center axis of said proximal end opening is coincidental to said barrel center axis.

38. The apparatus of claim 37, wherein said valve is movable about a rotation axis, and wherein said rotation axis is coincidental to said barrel center axis.

39. The apparatus of claim 38, wherein said center axis of said proximal end opening of said one port of said second set of ports is co-axial with said rotation axis.

40. The apparatus of claim 37, wherein said center axes of said end openings of said ports comprising said first set of ports are coincidental and non-overlapping with said rotation axis.

41. The apparatus of claim 37, wherein said rotation axis is co-axial with said barrel center axis, and wherein each of said ports of said first and second set of ports are disposed within said valve in non-overlapping relation to said rotation axis.

42. The apparatus of claim 35, wherein said ports comprising said second set of ports comprises an end opening, wherein each of said end openings of said ports comprising said second set of ports comprises a center axis, and wherein center axes of distal end openings of said ports comprising said second set of ports are coincidental to center axes of interfacing end openings of ports comprising said first set of ports.

43. The apparatus of claim 1, further comprising:
a tubular member extending through at least a portion of said barrel.

44. The apparatus of claim 43, wherein said plunger is slidably disposed on said tubular member.

45. The apparatus of claim 44, further comprising:
a sealing member interconnected about a proximal end of said plunger, wherein said sealing member slidably engages an external surface of said tubular member and an internal surface of said barrel.

46. The apparatus of claim 45, wherein said tubular member defines a portion of said first medical liquid delivery line.

47. The apparatus of claim 45, wherein said first medical liquid delivery line extends through at least a portion of said tubular member.

48. The apparatus of claim 45, further comprising:
a ring member fixedly interconnected about a distal end of said tubular member, wherein said ring member at least slidably engages an internal surface of said plunger.

49. The apparatus of claim 48, wherein said ring member sealably engages an internal surface of said plunger.

50. The apparatus of claim 48, wherein said ring member comprises a microbial barrier material.

51. The apparatus of claim 50, wherein said microbial barrier material comprises open-cell foam.

52. The apparatus of claim 48, further comprising:
a flexible sheath interconnected to said distal end of said barrel and said proximal end of said plunger, wherein said flexible sheath is adapted for co-movement relative to said plunger.

53. The apparatus of claim 52, further comprising:
an inner chamber defined by at least said flexible sheath, an internal surface of said barrel, an external surface of said plunger, and a distal surface of said sealing member.

54. The apparatus of claim 53, further comprising:
a plunger chamber defined by at least a proximal surface of said ring member, an internal surface of said plunger and an external surface of said tubular member.

55. The apparatus of claim 1, further comprising a check valve interconnected to said first medical liquid delivery line between said proximal end and a distal end thereof.

* * * * *